US008258248B2

(12) United States Patent
Jennings et al.

(10) Patent No.: US 8,258,248 B2
(45) Date of Patent: Sep. 4, 2012

(54) PREPARATION OF CATIONIC TERPOLYMERS AND PERSONAL CARE COMPOSITIONS COMPRISING SAID TERPOLYMERS

(75) Inventors: John Jennings, Moycullen (IE); Xian-Zhi Zhou, Leonia, NJ (US)

(73) Assignee: BASF SE, Ludwigshafen (DE)

( * ) Notice: Subject to any disclaimer, the term of this patent is extended or adjusted under 35 U.S.C. 154(b) by 703 days.

(21) Appl. No.: 12/317,023

(22) Filed: Dec. 18, 2008

(65) Prior Publication Data

US 2009/0175804 A1 Jul. 9, 2009

Related U.S. Application Data

(60) Provisional application No. 61/008,350, filed on Dec. 20, 2007.

(51) Int. Cl.
*C08F 26/04* (2006.01)
(52) U.S. Cl. .................... 526/279; 424/70.122
(58) Field of Classification Search .................. 526/279; 424/70.122
See application file for complete search history.

(56) References Cited

U.S. PATENT DOCUMENTS

| | | | | |
|---|---|---|---|---|
| 3,700,623 | A | 10/1972 | Kelm | 260/80.3 |
| 3,833,331 | A | 9/1974 | Springs | 425/253 |
| 3,912,808 | A | 10/1975 | Sokol | 424/71 |
| 3,968,037 | A | 7/1976 | Morgan et al. | 210/47 |
| 3,986,825 | A | 10/1976 | Sokol | 8/10.1 |
| 4,027,008 | A | 5/1977 | Sokol | 424/62 |
| 4,341,887 | A | 7/1982 | Buriks et al. | 526/263 |
| 4,354,006 | A | 10/1982 | Bankert | 525/359.5 |
| 4,419,498 | A | 12/1983 | Bankers | 525/426 |
| 4,419,500 | A | 12/1983 | Bankert | 525/540 |
| 5,147,411 | A | 9/1992 | Töpfl | 8/606 |
| 5,338,541 | A | 8/1994 | Matz et al. | |
| 5,465,792 | A | 11/1995 | Dawson et al. | 166/295 |
| 5,476,522 | A | 12/1995 | Kerr et al. | 44/626 |
| 5,622,647 | A | 4/1997 | Kerr et al. | 525/194 |
| 6,169,058 | B1 | 1/2001 | Le et al. | 507/222 |
| 6,207,778 | B1 | 3/2001 | Jachowicz et al. | |
| 6,323,306 | B1 | 11/2001 | Song et al. | 528/342 |
| 6,383,994 | B1 | 5/2002 | Maurin et al. | 510/119 |
| 6,383,995 | B1 | 5/2002 | Maurin et al. | 510/119 |
| 6,383,996 | B1 | 5/2002 | Maurin et al. | 510/119 |
| 6,403,542 | B1 | 6/2002 | Maurin et al. | 510/122 |
| 6,432,894 | B1 | 8/2002 | Maurin et al. | 510/122 |
| 6,926,900 | B1 | 8/2005 | Maurin et al. | 424/401 |
| 2003/0059382 | A1 | 3/2003 | Brandt et al. | |
| 2004/0105832 | A1 | 6/2004 | Fack et al. | 424/70.13 |
| 2005/0025736 | A1 | 2/2005 | Jachowicz et al. | |
| 2007/0185281 | A1* | 8/2007 | Song et al. | 525/375 |
| 2010/0303750 | A1* | 12/2010 | Koroskenyi et al. | 424/70.12 |

FOREIGN PATENT DOCUMENTS

| | | |
|---|---|---|
| JP | 6108382 | 4/1994 |
| WO | 9406403 | 3/1994 |
| WO | 01/41719 | 6/2001 |

OTHER PUBLICATIONS

International Search Report dated Mar. 30, 2009.
English Language Abstract for Publication No. JP6108382, Publication Date Apr. 19, 1994.

* cited by examiner

*Primary Examiner* — Margaret Moore
(74) *Attorney, Agent, or Firm* — Shiela A. Loggins

(57) ABSTRACT

The present invention is directed to cationic terpolymers, methods to make them, and the use of compositions containing said terpolymers in personal care compositions. The polymers are useful in personal care applications. The cationic terpolymers of this present invention provide the extra conditioning benefits required in a personal care product. These cationic terpolymers also contribute useful conditioning properties to hair-care and skin-care products.

23 Claims, No Drawings

PREPARATION OF CATIONIC TERPOLYMERS AND PERSONAL CARE COMPOSITIONS COMPRISING SAID TERPOLYMERS

This application takes the benefit of U.S. Provisional Application Nos. 61/008,350, filed Dec. 20, 2007, herein incorporated entirely by reference.

BACKGROUND OF THE INVENTION

The present invention relates to multifunctional water-soluble cross-linked cationic terpolymers and personal care compositions comprising these multifunctional water-soluble cross-linked cationic terpolymers. The present invention also relates to methods for using such cationic terpolymers to treat various substrates; for example, hair, skin, etc.

Cationic polymers have been used extensively in water treatment, paper making, mineral processing, petroleum recovery, textile dyeing, cosmetics and pharmaceuticals. Among the most important and extensively used cationic polymers are the quaternary ammonium polymers of diallyldimethylammonium chloride (DADMAC). These polymers are also known to be used in personal care applications.

Polymerization of DADMAC is typically carried out in aqueous solution using a free radical initiator such as a persulfate salt. Several approaches have been tried to increase the molecular weight of DADMAC polymers, including polymerization with added inorganic salts, polymerization in oil-in-water emulsions or suspended droplets, and addition of cross-linkers during polymerization. These methods are well known to those skilled in the art.

U.S. Pat. No. 3,968,037 discloses that cationic polymers made by inverse emulsion polymerization with cross-linking and branching agents are used as flocculants and for the treatment of activated sewage sludge.

Cationic polymers have been used extensively in home and personal care, water treatment, papermaking, mineral processing, petroleum recovery, fabrics, and pharmaceuticals. Among the most important and extensively used cationic polymers are the quaternary ammonium polymers of diallyldialkyl ammonium compounds. In fact, homopolymers of diallyldimethyl ammonium chloride (DADMAC) are well known in the home and personal care industry as polyquaternium 6, and are used extensively in skin and hair care applications.

The use of homo- and copolymers of diallyldimethylammonium salts in personal care applications has been disclosed in several U.S. patents.

The present invention relates to novel water-soluble, cross-linked, and cationic terpolymers, for example of diallyidimethylammonium chloride (DADMAC) and diallylamine (DAA), that provide excellent conditioning properties. The terpolymers of this present invention provide the extra conditioning benefits required in a personal care product. They also contribute useful properties to skin care products.

U.S. Pat. Nos. 3,700,623 and 3,833,531 teach making certain acid stabilized poly(diallylamine)-epihalohydrin resins, the disclosure of which is herein incorporated by reference. The obtained resin had a tendency to gel on standing. The resin solution was therefore stabilized against gelation by adding enough water-soluble acid (e.g. HCl) to adjust the pH to about 2. The acid-stabilized poly(diallylamine)-epichlorohydrin resins were reactivated prior to use by addition of a base (e.g. NaOH) to adjust pH to above 7. The half-reacted epihalohydrin entities of the alkaline curing resins impart epoxy functionality for crosslinking reactions after being reactivated by addition of alkaline base prior to use. These polymers are insoluble after crosslinking.

U.S. Pat. Nos. 4,354,006, 4,419,498 and 4,419,500 teach a process for making certain poly(DAA-ECH) polymers by reacting a diallylamine (DAA) polymer first with an allyl halide and then with hypohalous acid to convert the allyl substituents to halohydrin moieties, the disclosures of which are herein incorporated by reference.

JP 6,108,382 discloses another way to make certain poly (diallylamine)-epihalohydrin polymers. A diallylamine-epihalohydrin halo salt monomer is first prepared by reacting diallylamine with an epihalohydrin (typically epichlorohydrin, ECH) and then neutralizing with a halo acid (typically HCl).

U.S. Pat. No. 5,147,411 discloses a method to prepare the DM-ECH monomers (3-halo-2-hydroxypropyl)diallylamine and (2,3-epoxypropyl)diallylamine, and their quaternary ammonium salts, the disclosure of which is herein incorporated by reference.

U.S. Pat. No. 4,341,887 discloses that the reaction product of diallylamine and epichlorohydrin (3-chloro-2-hydroxypropyl)diallylamine (a DAA-ECH monomer), can be converted to N,N-diallyl-3-hydroxy-azetidinium chloride (DM-ECH azetidinium monomer) by heating in the presence of water, the disclosure of which is herein incorporated by reference.

The above-reviewed patents involve use of an epihalohydrin as a reactive compound to react with DAA monomer or a DAA polymer. Since an epihalohydrin (e.g. epichlorohydrin) is a difunctional reactive crosslinker, highly crosslinked insoluble end products are obtained when fully reacted with equivalent high DAA-containing (i.e. >5%) polymers.

Commonly assigned U.S. Pat. No. 6,323,306, the disclosure of which is incorporated by reference, discloses a method to prepare certain water-soluble cationic polymers by reacting an amino-functionalized DADMAC polymer with a difunctional reactive crosslinker. The reactive crosslinkers include epihalohydrin and other polyfunctional compounds that can be used to cross-link the diallylamine polymers. The patent is limited to a DAA content of less than 5% to prevent formation of undesirable insoluble products which can be caused by excessive crosslinking due to use of the difunctional reactive crosslinker.

U.S. Pat. Nos. 3,912,808, 3,986,825, and U.S. Pat. No. 4,027,008 disclose DADMAC homopolymers and copolymers with acrylamide derivatives in hair care compositions, the disclosures of which are herein incorporated by reference.

U.S. Pat. Nos. 5,622,647 and 5,476,522 disclose DADMAC and vinyltrialkoxysilane copolymers for dewatering in the mining industry, the disclosures of which are herein incorporated by reference.

Copending U.S. application Ser. No. 11/595,152, filed on Nov. 9, 2006, discloses the preparation of functionalized cationic polymers and their application in personal care, the disclosure of which is herein incorporated by reference.

Copending U.S. Provisional Application No. 60/899,675, filed on Feb. 6, 2007, discloses the preparation of polysiloxane block copolymers, the disclosure of which is herein incorporated by reference.

U.S. Pat. Nos. 6,383,995, 6,432,894, 6,403,542, and 6,383,994 discloses compositions for washing keratin-based materials, the disclosures of which are herein incorporated by reference.

U.S. Pat. No. 6,383,996 discloses antidandruff compositions for treating the hair and scalp, the disclosure of which is herein incorporated by reference.

U.S. Pat. No. 6,383,993 discloses compositions for washing keratin-based materials comprising a cationic galactomannan gum and an acrylic terpolymer, the disclosure of which is herein incorporated by reference.

U.S. Pat. No. 6,926,900 discloses antidandruff compositions for treating the hair and scalp comprising an acrylic terpolymer, the disclosure of which is herein incorporated by reference.

U.S. Pat. No. 6,169,058 discloses compositions and methods for hydraulic fracturing, the disclosure of which is herein incorporated by reference.

U.S. Pat. No. 5,465,792 discloses methods of controlling production of excess water in oil and gas wells, the disclosure of which is herein incorporated by reference.

US 2004/0105832 discloses cosmetic compositions containing a fructan and a cationic polymer, the disclosure of which is herein incorporated by reference.

WO 2001/41719 discloses cosmetic compositions containing a quaternary silicon and a pearling agent.

Accordingly, there is still a need for water-soluble, cross-linked, and cationic terpolymers that provide excellent conditioning properties in personal care products. The cationic terpolymers of this present invention provide the extra conditioning benefits required in a personal care product. These cationic terpolymers also contribute useful properties to skin care products.

SUMMARY OF THE INVENTION

The present invention is directed to cationic terpolymers, methods to make them, and the use of compositions containing said terpolymers in personal care compositions. The polymers are useful in personal care applications. The cationic terpolymers of this present invention provide the extra conditioning benefits required in a personal care product. These cationic terpolymers also contribute useful conditioning properties to hair-care and skin-care products.

Another embodiment of the instant invention is a method for the conditioning treatment of mammalian keratin-containing fibers, wherein said method comprises contacting said fibers with an effective amount of a personal care composition or formulation comprising one or more cationic terpolymers of formula (I).

Another embodiment of the instant invention is a method for the conditioning treatment of mammalian skin, wherein said method comprises contacting said skin with an effective amount of a personal care composition or formulation comprising one or more cationic terpolymers of formula (I).

DETAILED DESCRIPTION OF THE INVENTION

The present invention provides a personal care composition comprising:
(a) an effective amount of at least one cationic terpolymer of formula (I)

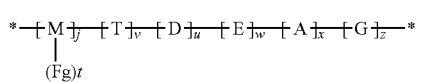
(I)

wherein
j, t, u, v, w, x, and z represent the percentage by weight that each repeating unit or derived monomer is contained within the terpolymer;

* is a terminal group, for example a catalyst residue;
j, t, u, v, w, x, and z add up to total 100 percent and are based on weight of the terpolymer;
j, u and x are independently from 0.0001 to 39.9997% based on weight of the terpolymer;
j+u+x is less than or equal to 39.9999% percent based on the weight of the terpolymer;
w is from about 0.0001% to about 20% by weight of the terpolymer;
t is from about 0% to about 20% by weight of the terpolymer;
z and v are independently from about 0.0001 to about 60% based on weight of the terpolymer;
z+v is equal to or greater than 60 percent based on the weight of the terpolymer;
E is derived from a difunctional siloxane monomer of formula (II)

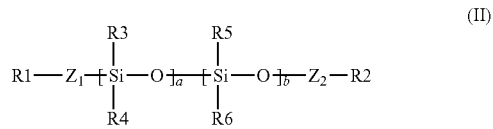

R1 and R2 independently are a polymerizable function from the group of the vinylically unsaturated compounds which is suitable for the synthesis of polymeric structures by a free-radical route or by condensation and represents vinyl, allyl, methallyl, methylvinyl, acryloyl (CH2=CH—CO—), methacryloyl (CH2=C[CH3]—CO—), crotonyl, senecionyl, itaconyl, maleyl, fumaryl, epoxy or styryl radicals;
Z1 is a direct bond or a bridging group selected from the group consisting of —O—, —((C1-C50)alkylene), —((C6-C30)arylene)-, —((C5-C8)cycloalkylene)-, —((C1-C50)alkenylene)-, -(polypropylene oxide)n-, -(polyethylene oxide)o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;
Z2 is a direct bond or a bridging group selected from the group consisting of —((C1-C50)alkylene), —((C6-C30) arylene)-, —((C5-C8)cycloalkylene)-, —((C1-C50)alkenylene)-, -(polypropylene oxide)n-, -(polyethylene oxide) o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;
R3, R4, R5, and R6 are independently straight or branched alkyl chain of 1 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl groups of 1 to 4 carbon atoms; or said alkyl substituted by one or more —OH, —OCO—$R_{10}$, —O$R_{10}$, or —$NH_2$ groups or mixtures thereof; or said alkyl interrupted by one or more —O—, —NH— or —$NR_{10}$— groups or mixtures thereof and which can be unsubstituted or substituted by one or more —OH, —O$R_{10}$ or —$NH_2$ groups or mixtures thereof; or $OR_{11}$;
$R_{10}$ is straight or branched chain alkyl of 1 to 24 carbon atoms or phenyl or benzyl;
$R_{11}$ is straight or branched chain alkyl of 1 to 24 carbon atoms or phenyl or benzyl; or said alkyl substituted by one or more —OH, —OCO—$R_{10}$, —O$R_{10}$, or —$NH_2$ groups or mixtures thereof; or said alkyl interrupted by one or more —O—, —NH— or —NR$_{10}$— groups or mixtures thereof and which can be unsubstituted or substituted by one or more —OH, —OR$_{10}$ or —NH$_2$ groups or mixtures thereof;

a and b represent stoichiometric coefficients which amount independently of one another to from 1 to 5000; or E is derived from a difunctional polypropylene glycol or polyethylene glycol monomer of formula (VI);

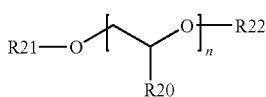
(VI)

R20 is hydrogen or methyl; R21 and R22 are independently vinyl, allyl, methallyl, methylvinyl, acryloyl (CH2=CH—CO—), methacryloyl (CH2=C[CH3]—CO—), crotonyl, senecionyl, itaconyl, maleyl, fumaryl, epoxy or styryl radicals;

Fg is the residue from at least one functional reactant grafted onto a cationic amino base polymer;

G and T are independently derived from a monomer selected from the group consisting of diallyidimethyl ammonium chloride (DADMAC), diallyldimethyl ammonium bromide, diallyldimethyl ammonium sulfate, diallyidimethyl ammonium phosphates, dimethallyldimethyl ammonium chloride, diethylallyl dimethyl ammonium chloride, diallyl di(beta-hydroxyethyl) ammonium chloride, and diallyl di(beta-ethoxyethyl) ammonium chloride;

M, D and A are independently derived from a monomer of formula (III)

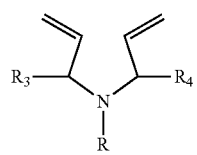
(III)

where R, R$_3$ and R$_4$ are, independently of each other, hydrogen or C$_1$-C$_4$alkyl; and (b) a cosmetically acceptable adjuvant.

Another embodiment of the instant invention is M, D and A that are independently derived from a monomer selected from the group consisting of diallylamine, 2,2'-dimethyl diallylamine, 2,2'-diethyl diallylamine, 2,2'-diisopropyl diallylamine, 2,2'-dipropyl diallylamine, 2,2'-diisobutyl diallylamine, N-methyl diallylamine, N-ethyl diallylamine, 2,2'-dimethyl-N-methyl diallylamine, 2,2'-diethyl-N-methyl diallylamine, 2,2'-diisopropyl-N-methyl diallylamine, 2,2'-dipropyl-N-methyl diallylamine, 2,2'-dimethyl-N-ethyl diallylamine, and 2,2'-diethyl-N-ethyl diallylamine.

Another embodiment of the instant invention is M, D and A that are independently derived from a monomer selected from the group consisting of diallylamine and N-methyl diallylamine.

Another embodiment of the instant invention is M, D and A that are derived from diallylamine.

Another embodiment of the instant invention is G and T that are independently derived from a monomer selected from the group consisting diallyldimethyl ammonium chloride, diallyldimethyl ammonium sulfate, dimethallyldimethyl ammonium chloride, diethylallyl dimethyl ammonium chloride, diallyl di(beta-hydroxyethyl) ammonium chloride, and diallyl di(beta-ethoxyethyl) ammonium chloride.

Another embodiment of the instant invention is G and T that are derived from diallyldimethyl ammonium chloride.

Another embodiment of the instant invention is E that is derived from a difunctional siloxane monomer of formula (II)

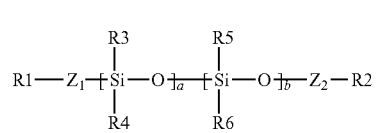
(II)

R1 and R2 independently are vinyl, allyl, methallyl, methylvinyl, acryloyl (CH2=CH—CO—), methacryloyl (CH2=C[CH3]—CO—), or epoxy;

Z1 is a direct bond or a bridging group selected from the group consisting of —O—, —((C1-C18)alkylene), —((C6-C10)arylene)-, —((C5-C8)cycloalkylene)-, -(polypropylene oxide)n-, -(polyethylene oxide)o-, -(polypropylene-oxide)n (polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;

Z2 is a direct bond or a bridging group selected from the group consisting of —O—, —((C1-C18)alkylene), —((C6-C10)arylene)-, —((C5-C8)cycloalkylene)-, -(polypropylene oxide)n-, -(polyethylene oxide)o-, -(polypropylene-oxide)n (polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;

R3, R4, R5, and R6 are independently straight or branched alkyl chain of 1 to 12 carbon atoms, cycloalkyl of 5 to 12 carbon atoms, phenyl; or said alkyl substituted by one or more —OH, —OCO—R$_{10}$, —OR$_{10}$, or —NH$_2$ groups or mixtures thereof; or said alkyl interrupted by one or more —O—, —NH— or —NR$_{10}$— groups or mixtures thereof and which can be unsubstituted or substituted by one or more —OH, —OR$_{10}$ or —NH$_2$ groups or mixtures thereof; or OR$_{11}$;

R$_{10}$ is straight or branched chain alkyl of 1 to 24 carbon atoms or phenyl or benzyl;

R$_{11}$ is straight or branched chain alkyl of 1 to 12 carbon atoms;

a and b represent stoichiometric coefficients which amount independently of one another to from 1 to 5000; or E is derived from a difunctional polypropylene glycol or polyethylene glycol monomer of formula (VI);

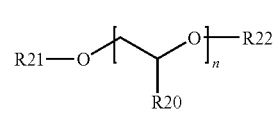
(VI)

R20 is hydrogen or methyl; R21 and R22 are independently allyl, methallyl, acryloyl (CH2=CH—CO—), methacryloyl (CH2=C[CH3]—CO—) or epoxy; and n is 1 to 5000.

Another embodiment of the instant invention is E that is derived from a difunctional siloxane monomer of formula (II)

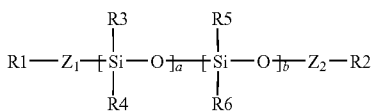  (II)

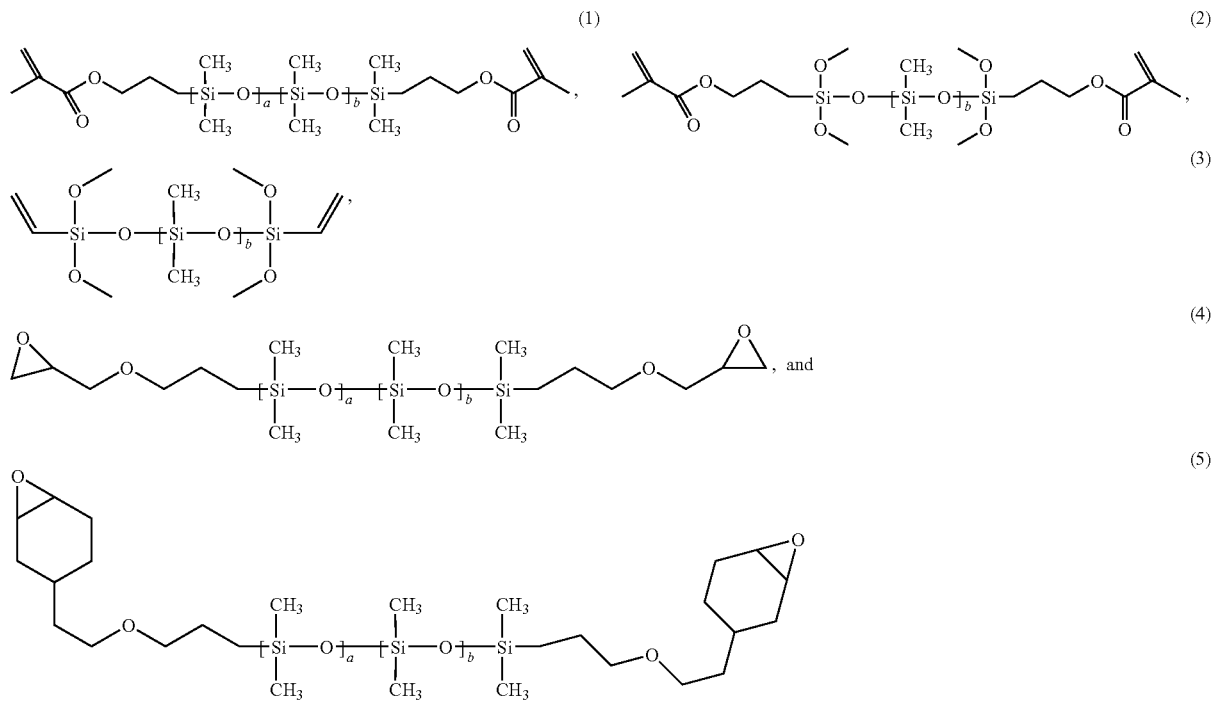

R1 and R2 independently are vinyl, allyl, methallyl, methylvinyl, acryloyl (CH2=CH—CO—), methacryloyl (CH2=C[CH3]—CO—), or epoxy;

Z1 is a direct bond or a bridging group selected from the group consisting of —O—, —((C1-C12)alkylene, —((C5-C8)cycloalkylene)-, —((C1-C10)alkyl)-(Si(OCH3)2)- and —(Si(OCH3)2)-;

Z2 is a direct bond or a bridging group selected from the group consisting of —O—, —((C1-C12)alkylene, —((C5-C8)cycloalkylene)-, —((C1-C10)alkyl)-(Si(OCH3)2)- and —(Si(OCH3)2)-;

R3, R4, R5, and R6 are independently straight or branched alkyl chain of 1 to 12 carbon atoms, phenyl; or $OR_{11}$;

$R_{11}$ is straight or branched chain alkyl of 1 to 12 carbon atoms;

a and b represent stoichiometric coefficients which amount independently of one another to from 1 to 5000; or E is derived from a difunctional polypropylene glycol or polyethylene glycol monomer of formula (VI);

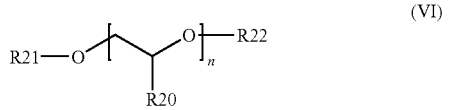  (VI)

R20 is hydrogen or methyl; R21 and R22 are independently acryloyl (CH2=CH—CO—), methacryloyl (CH2=C[CH3]—CO—) or epoxy and n is 1 to 2000.

Another embodiment of the instant invention is E that is derived from a difunctional siloxane monomer selected from the group consisting of wherein a and b are independently 1 to 1000; or E is derived from a difunctional polypropylene glycol or polyethylene glycol monomer selected from the group consisting of

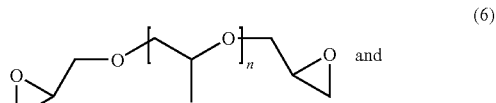  (6)

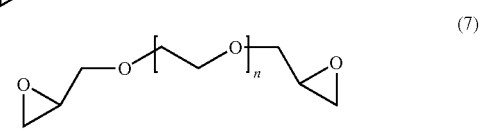  (7)

wherein n is 1 to 500.

An amino-group containing base polymer of formula prepared for example as described above, is functionalized or modified by reacting it with at least one reactive functional compound (grafting agent and/or crosslinking agent) (2). Compounds with groups that can react with the amino-functional groups in the base polymer can be used to impart the properties or functionality of the grafting agent used. Suitable reactive compounds for grafting or crosslinking include, but are not limited to, epoxy compounds, haloalkyl compounds, isocyanate compounds and compounds containing activated olefinic double bonds. Suitable reactive compounds for grafting or crosslinking in non-aqueous systems also include acid halides and anhydrides.

In one embodiment of the invention, the functional reactive compound or grafting agent (2) used is an epoxy or halohydrin compound to give the functional group Fg as

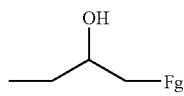

which contains a

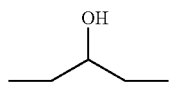

linkage connecting its residual Fg to the amino nitrogen of the base polymer.

Examples of monofunctional epoxy compounds suitable for grafting include, but are not limited to, the following glycidyl compounds: mono-(2,3-epoxy)propylether-terminated polydimethyl-siloxanes, 3-glycidoxypropyltrimethoxysilane, 1-oxy-2,2,6,6,-tetramethyl-4-glycidyloxypiperidine, glycidyl isopropyl ether, glycidyl isobutyl ether, glycidyl heptyl ether, glycidyl 2-methylphenyl ether, glycidyl hexadecyl ether, glycidyl hexadecafluorononyl ether, glycidyl 4-nonylphenyl ether, 1,2-epoxydodecane, 1,2-epoxyoctadecane, 1,2-epoxy-3-phenoxy propane, glycidyltrimethylammonium chloride, glycidyl 3-nitrobenzenesulfonate, and the like.

Non-limiting examples of polyfunctional epoxy compounds include, but are not limited to, ethylene glycol diglycidyl either (EGDE); diglycidyl ether; 1,2,3,4-diepoxybutane; 1,2,5,6-diepoxyhexane; poly(propylene glycol) diglycidyl ether (PPGDE); 1,4-butanediol diglycidyl ether, 3-bis(glycidyloxy)methyl-1,2-propanediol, bisphenol A diglycidyl ether (BADGE), poly(phenyl glycidyl ether-co-formaldehyde), glycerol propoxylate tri-glycidyl ether, N,N-diglycidyl-4-glycidyloxyaniline, triglycidyl isocyanurate and the like. Preferred epoxy crosslinkers are bisphenol A diglycidyl ether and ethylene glycol diglycidyl ether.

When monofunctional epoxy compounds are reacted with an amine portion of the cationic terpolymer of formula (I), functionalized cationic polymers such as those of the structure (V) can be obtained and wherein the schematic representation below shows only a DAA/DADMAC segment of the cationic terpolymer:

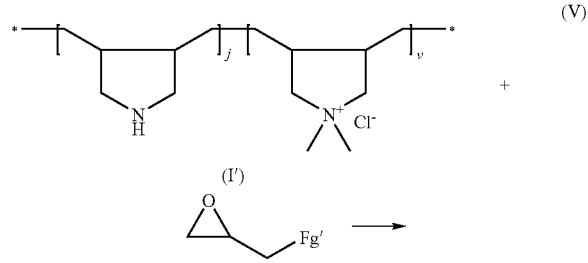

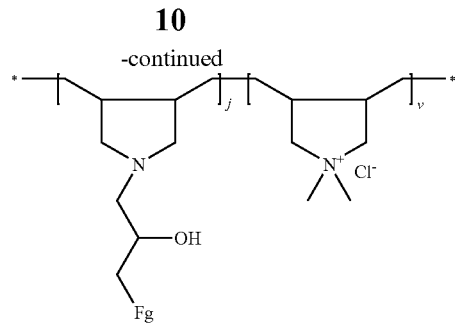

where Fg=H, $C_1$ to $C_{30}$ alkyl or
—O—R

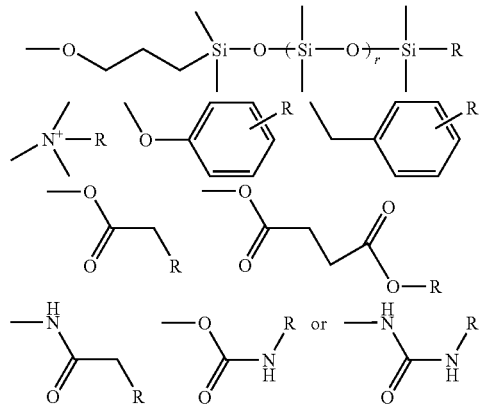

wherein R is hydrogen, C1 to C30 alkyl, C1 to C30 perfluoroalkyl, 1 to 1500 ethoxy units, 1 to 1500 propoxy units, 1 to 1500 mixed ethoxy-propoxy units, j and v are defined previously, and r is a number from 1 to 100.

Certain epoxy compounds in halohydrin form can also be used as reactive compounds for functionalizing the amino cationic base polymer. Examples of these include, but are not limited to, 3-chloro-2-hydroxypropyl-dimethyldodecylammonium chloride and 3-chloro-2-hydroxypropyl-dimethyloctadecylammonium chloride (QUAB® 342 & QUAB® 426 from Degussa). Thus, in the functionalized cationic polymer of formula (V), Fg will be the residue from reacting 3-chloro-2-hydroxypropyl-dimethyldodecylammonium chloride or 3-chloro-2-hydroxypropyl-dimethylocta-decylammonium chloride.

Haloalkyl compounds can also be used as reactive compounds for functionalizing the base amino cationic polymer. Examples of mono-functional haloalkyl compounds suitable for grafting include, but are not limited to, chloroethane, bromoethane, 1-chloropropane, 1-chlorobutane, chloroacetic acid and its salts, dichloride-substituted cyanuric chloride and the like. Preferred haloalkyl reactants are bromoethane and chloroethane because of their low cost. Thus, in the functionalized cationic polymer of formula (Ia and Ib), Fg will be the residue of a haloalkyl compound to give the functional group Fg as

which contains a

linkage connecting its residual Fg to the amine nitrogen of the cationic terpolymer of formula (I).

Examples of dihaloalkyl compounds that can be used to graft or crosslink cationic base polymers containing primary or secondary amino groups include, but are not limited to, 1,2-dichloroethane, 1,2-dibromoethane, 1,3-dichloropropane, 1,4-dichlobutane, 1,6-dichlorohexane, 1,10-dichlorodecane and the like. Preferred dihaloalkyl compounds are 1,2-dibromoethane and 1,2-dichloroethane.

Trihalo compounds such as cyanuric chloride and its chloro-substituted derivatives may also be employed. As is well known, replacement of each halogen on cyanuric chloride is progressively more difficult. This may be exploited to introduce dihalotriazinyl functional groups into a cationic base polymer, with subsequent reaction to introduce further functionality.

Examples of other difunctional reactants to graft or crosslink cationic base polymers include, but are not limited to, N,N'-methylenebisacrylamide (MBA), N,N'-ethylenebisacrylamide, epichlorohydrin, ethylene glycol diacrylate, diethylene glycol diacrylate, poly(ethylene glycol) diacrylate, poly(propylene glycol) diacrylate and the like. MBA is a preferred crosslinking agent.

Depending on the reactant charge ratio, one can preferentially react just one functional group of a difunctional reactant. When used as a crosslinker for the cationic base polymer, only low amounts (0.1 to 3 weight percent) will normally be employed.

Compounds containing activated olefinic double bonds can also be used to graft or crosslink cationic base polymers containing primary or secondary amino groups via a Michael addition. Examples of monofunctional compounds suitable for use in a Michael addition include, but are not limited to, (meth)acrylamide, (meth)acrylonitrile, esters of (meth)acrylic acid such as methyl acrylate, butyl acrylate, lauryl acrylate(LA), 2-hydroxyethyl acrylate (HEA), N-substituted (meth)acrylamides such as N,N-dimethylacrylamide and N-isopropylacrylamide (NIPA). Preferred compounds include 2-hydroxyethyl acrylate, N,N-dimethylacrylamide and N-isopropylacrylamide.

Thus, in the previously mentioned functionalized cationic polymers of formulae (Ia and Ib),

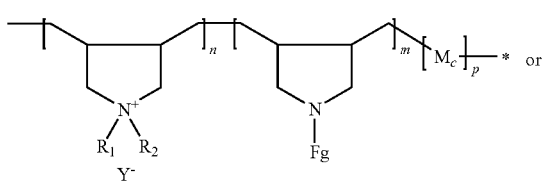

(Ia)

(Ib)

Fg will be the residue from reacting at least one compound containing an activated olefinic double bond, wherein said compound is an acrylate compound, to give the functional group Fg as which contains a linkage connecting its residual Fg' to an amino nitrogen of a cationic base polymer.

When said compound is an acrylamide, it gives the functional groups Fg as which contains a linkage connecting its residual Fg groups to an amino nitrogen of a cationic base polymer, wherein the Fg groups are the same or different.

When said compound is acrylonitrile or methacrylonitrile, it gives the functional group Fg as Anhydride compounds can also graft to base polymers containing primary or secondary amino groups. Examples of suitable anhydride compounds for reactant (II) include, but are not limited to, phthalic, maleic, succinic, pyromellitic and tetrahydrophthalic anhydrides, 2-dodecen-1-yl succinic anhydride and the like. In one embodiment the anhydride compound is 2-dodecen-1-yl succinic anhydride.

The reactive compound is used in an amount ranging from about 0.02 to about 3.0 moles, preferably from 0.2 to 1.0 moles, of functional groups in the reactive compound for each mole of reactive amine present in the base polymer. The equivalent ratio of reactive compound to base polymer may change depending on the desired properties for the final polymer. The reactive compound is used in an amount which is effective to give a product certain desired properties after being fully reacted with the amino functional groups in the base polymer. More than one reactive compound may be reacted, simultaneously or sequentially in any order, with the base polymer.

The grafting reaction can be carried out in an aqueous medium or in the same reaction medium (e.g., water-in-oil emulsion) as is used for preparing the base polymer in step (a). The reaction is preferably carried out in aqueous medium at a pH of from about 7 to about 11, preferably from 7.5 to 9.5, and at a temperature from about 0 to about 100° C., preferably from 20 to 80° C. The solids concentration of the base polymer in the reaction medium prior to reaction can be, by weight, from 1% to about 60%, preferably from 10% to 25% for a solution of the base polymer, and preferably from 20 to 50% for an emulsion or dispersion of the base polymer.

The preparation of the cationic terpolymers of formula (I) can be carried out using various polymerization techniques such as solution, emulsion, microemulsion, inverse emulsion, and/or bulk polymerization, as well as other technologies that are available to those who are skilled in the art. The polymerizations can be carried out with or without free radical initiators and with various initiator concentrations. The cationic terpolymers can also be prepared in such a way that the architecture of the resulting terpolymers is random, block, alternating or core-shell, and with or without the use of polymerization regulators such as nitroxyl ethers or other types of nitroxyl radicals.

Examples of the suitable initiators include, but are not limited to, persulfates such as ammonium persulfate (APS); peroxides such as hydrogen peroxide, t-butyl hydroperoxide, and t-butyl peroxy pivalate; azo initiators such as 2,2'-azobis (2-amidinopropane) dihydrochloride, 4,4'-azobis-4-cyanovaleric acid and 2,2'-azobisisobutyronitrile, and redox initiator systems such as t-butyl hydroperoxide/Fe(II) and ammonium persulfate/bisulfite. Aqueous solution polymerization using ammonium persulfate (APS) is the preferred method for preparing the amino-functionalized base cationic polymer of the preferred monomers DADMAC and DAA (or MDAA).

The amount of the free radical initiator used in the polymerization process depends on the total monomer concentration and the type of monomers used, and may range from about 0.2 to about 5.0 wt % of total monomer charge to achieve more than 99% of total monomer conversion.

In one embodiment the polymerization is carried out in the substantial absence of oxygen. Oxygen can be removed from the reaction medium by applying vacuum with agitation or by purging with an inert gas such as nitrogen or argon. The polymerization can then be conducted under a blanket of the inert gas.

A schematic representation of the inventive cationic terpolymers may be represented, for example, by formula (I'):

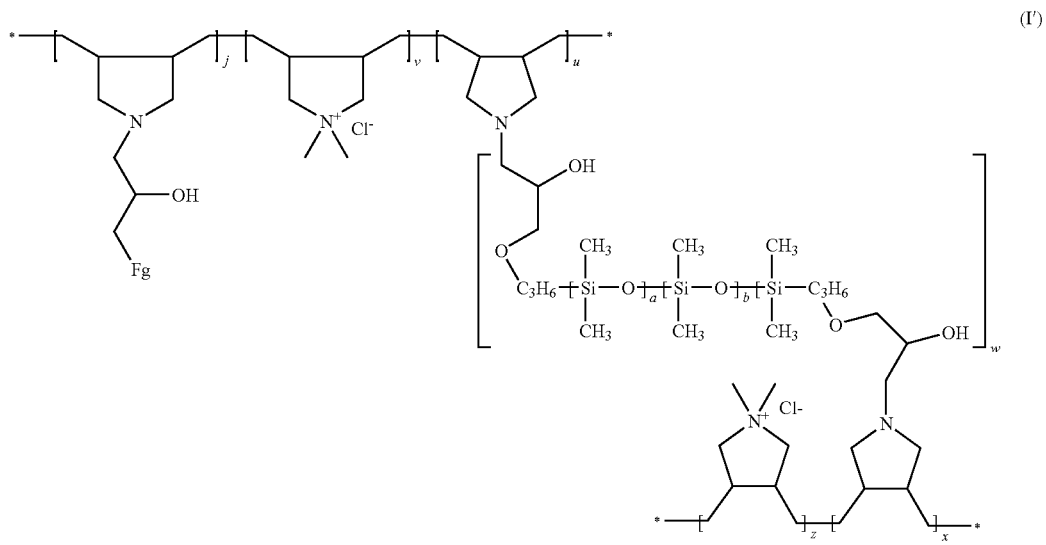

wherein M, D, and A of formula (I) are derived from diallylamine; T and G of formula (I) are derived from diallyldimethylammonium chloride; E is derived from the difunctional siloxane monomer of formula (4); j, v, u, w, x, a, b and z are defined above; and Fg is defined above.

According to the instant invention, the weight average molecular weight of the cationic terpolymers of formula (I) is from about 1,000 to about 10 million Daltons. Another embodiment of the instant invention is cationic terpolymers of formula (I) having a weight average molecular weight from about 25,000 to about 5 million Daltons. Another embodiment of the instant invention is cationic terpolymers of formula (I) having a weight average molecular weight from about 40,000 to about 4 million Daltons. Another embodiment of the instant invention is cationic terpolymers of formula (I) having a weight average molecular weight from about 50,000 to about 2 million Daltons.

The cationic terpolymers of formula (I) of the instant invention may be fully dissolved or partially dissolved in the personal are composition. The cationic terpolymers of formula (I) may be in the personal care composition in the form of particles.

Although there are no critical size limitations to the particles of the cationic terpolymers of formula (I), the particles having a size of about 0.001 to about 500 micrometers are particularly advantageous. Another embodiment of the instant invention is a particle size for the cationic terpolymers of formula (I) of about 0.01 to 300 micrometers. Another embodiment of the instant invention is a particle size for the cationic terpolymers of formula (I) of about 1 to 300 micrometers.

The instant cationic terpolymers can be present in various physical forms, i.e. solutions, dispersions, suspensions, granules, powders, beads, blocks, etc. In the case of liquid forms such as solutions, dispersions, suspensions, etc., the liquid phase can be aqueous and/or non-aqueous such as a dispersion in soybean oil, an ester or mineral oil. Preferred hydrocarbons as the non-aqueous solvent or dispersion medium include, but are not limited to, naphthol spirits, ESCAID 110 from Exxon, LPA 170 from Condea Vista and CONOSOL 200 from Penreco, an aromatics/paraffins/naphthalenes mixture.

The term "effective amount" means for example the amount necessary to achieve the desired effect.

The cationic terpolymers of formula (I) of the personal care compositions preferably comprise no more than about 50 weight percent of the composition; more preferably no more than about 25 weight percent of the personal care composition; even more preferably no more than about 7 weight percent; and still more preferably no more than about 5 weight percent. The cationic terpolymers of formula (I) of the personal care composition preferably comprise at least about 0.0001 weight percent of the personal care composition, more preferably at least about 0.01 weight percent, even more preferably at least about 0.1 weight percent, and still more preferably at least about 0.2 by weight of the composition.

The present personal care compositions may comprise further traditional additives, for example ultraviolet (UV) light absorbers and antioxidants.

Accordingly, the present invention further pertains to a personal care composition comprising
(a) an effective amount of at least one cationic terpolymer of formula (I)

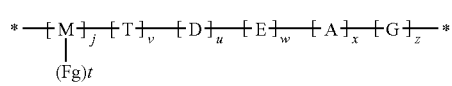

wherein
j, t, u, v, w, x, and z represent the percentage by weight that each repeating unit or derived monomer is contained within the terpolymer;
* is a terminal group, for example a catalyst residue;
j, t, u, v, w, x, and z add up to total 100 percent and are based on weight of the terpolymer;
j, u and x are independently from 0.0001 to 39.9997% based on weight of the terpolymer;
j+u+x is less than or equal to 39.9999% percent based on the weight of the terpolymer;
w is from about 0.0001% to about 20% by weight of the terpolymer;
t is from about 0% to about 20% by weight of the terpolymer;
z and v are independently from about 0.0001% to about 60% based on weight of the terpolymer;
z+v is equal to or greater than 60 percent based on the weight of the terpolymer;

E is derived from a difunctional siloxane monomer of formula (II)

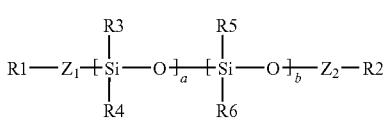

R1 and R2 independently are a polymerizable function from the group of the vinylically unsaturated compounds which is suitable for the synthesis of polymeric structures by a free-radical route or by condensation and represents vinyl, allyl, methallyl, methylvinyl, acryloyl (CH2=CH—CO—), methacryloyl (CH2=C[CH3]—CO—), crotonyl, senecionyl, itaconyl, maleyl, fumaryl, epoxy or styryl radicals;

Z1 is a direct bond or a bridging group selected from the group consisting of —O—, —((C1-C50)alkylene), —((C6-C30)arylene)-, —((C5-C8)cycloalkylene)-, —((C1-C50)alkenylene)-, -(polypropylene oxide)n-, -(polyethylene oxide)o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;

Z2 is a direct bond or a bridging group selected from the group consisting of —((C1-C50)alkylene), —((C6-C30)arylene)-, —((C5-C8)cycloalkylene)-, —((C1-C50)alkenylene)-, -(polypropylene oxide)n-, -(polyethylene oxide)o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;

R3, R4, R5, and R6 are independently straight or branched alkyl chain of 1 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl groups of 1 to 4 carbon atoms;
or said alkyl substituted by one or more —OH, —OCO—$R_{10}$, —$OR_{10}$, or —$NH_2$ groups or mixtures thereof; or said alkyl interrupted by one or more —O—, —NH— or —$NR_{10}$— groups or mixtures thereof and which can be unsubstituted or substituted by one or more —OH, —$OR_{10}$ or —$NH_2$ groups or mixtures thereof; or $OR_{11}$;
$R_{10}$ is straight or branched chain alkyl of 1 to 24 carbon atoms or phenyl or benzyl;
$R_{11}$ is straight or branched chain alkyl of 1 to 24 carbon atoms or phenyl or benzyl; or said alkyl substituted by one or more —OH, —OCO—$R_{10}$, —$OR_{10}$, or —$NH_2$ groups or mixtures thereof; or said alkyl interrupted by one or more —O—, —NH— or —$NR_{10}$— groups or mixtures thereof and which can be unsubstituted or substituted by one or more —OH, —$OR_{10}$ or —$NH_2$ groups or mixtures thereof;
a and b represent stoichiometric coefficients which amount independently of one another to from 1 to 5000; or E is derived from a difunctional polypropylene glycol or polyethylene glycol monomer of formula (VI);

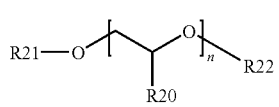

R20 is hydrogen or methyl; R21 and R22 are independently vinyl, allyl, methallyl, methylvinyl, acryloyl (CH2=CH—CO—), methacryloyl (CH2=C[CH3]—CO—), crotonyl, senecionyl, itaconyl, maleyl, fumaryl, epoxy or styryl radicals;

Fg is the residue from at least one functional reactant grafted onto a cationic amino base polymer;

G and T are independently derived from a monomer selected from the group consisting of diallyldimethyl ammonium chloride (DADMAC), diallyldimethyl ammonium bromide, diallyldimethyl ammonium sulfate, diallyldimethyl ammonium phosphates, dimethallyldimethyl ammonium chloride, diethylallyl dimethyl ammonium chloride, diallyl di(beta-hydroxyethyl) ammonium chloride, and diallyl di(beta-ethoxyethyl) ammonium chloride;

M, D and A are independently derived from a monomer of formula (III)

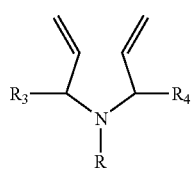

(III)

where R, $R_3$ and $R_4$ are, independently of each other, hydrogen or $C_1$-$C_4$alkyl;

(b) a cosmetically acceptable adjuvant; and
(c) at least one compound selected from the group consisting of ultraviolet light absorbers, antioxidants, tocopherol, tocopherol acetate, hindered amine light stabilizers, complex formers, optical brighteners, surfactants and polyorganosiloxanes.

The additional additives of present component (c) are for example those disclosed in co-pending U.S. application Ser. No. 09/830,788, filed May 1, 2001 and 09/830,787, filed May 1, 2001. The disclosures of these co-pending applications are hereby incorporated by reference. These applications are published as WO 00/25730 and WO 00/25731.

The UV (ultraviolet light) absorbers are for example selected from the group consisting of 2H-benzotriazoles, s-triazines, benzophenones, alpha-cyanoacrylates, oxanilides, benzoxazinones, benzoates and alpha-alkyl cinnamates.

The UV absorbers are, for example:
2,4,6-tris(2-hydroxy-4-octyloxyphenyl)-1,3,5-triazine;
2-(2,4-dihydroxyphenyl)-4,6-bis(2,4-dimethylphenyl)-1,3,5-triazine;
2,4-bis(2-hydroxy-4-propyloxyphenyl)-6-(2,4-dimethylphenyl)-1,3,5-triazine;
2-(2-hydroxy-4-octyloxyphenyl)-4,6-bis(4-methylphenyl)-1,3,5-triazine;
2-(2-hydroxy-4-dodecyloxyphenyl)-4,6-bis(2,4-dimethylphenyl)-1,3,5-triazine;
2-[2-hydroxy-4-(2-hydroxy-3-butyloxypropyloxy)phenyl]-4,6-bis(2,4-dimethylphenyl)-1,3,5-triazine;
2-[2-hydroxy-4-(2-hydroxy-3-octyloxypropyloxy)phenyl]-4,6-bis(2,4-dimethylphenyl)-1,3,5-triazine;
2-[2-hydroxy-4-(2-hydroxy-3-tridecyloxy-propyloxy)phenyl]-4,6-bis(2,4-dimethylphenyl)-1,3,5-triazine;
5-chloro-2-(2-hydroxy-3,5-di-tert-butylphenyl)-2H-benzotriazole;
2-(2-hydroxy-3-dodecyl-5-methylphenyl)-2H-benzotriazole;
5-chloro-2-(2-hydroxy-3-tert-butyl-5-methylphenyl)-2H-benzotriazole;
bis-(3-(2H-benzotriazol-2-yl)-2-hydroxy-5-tert-octyl)methane;
2-(2-hydroxy-3,5-di-tert-butylphenyl)-2H-benzotriazole;
2-(2-hydroxy-3,5-di-tert-amylphenyl)-2H-benzotriazole;
2-(2-hydroxy-3,5-di-alpha-cumylphenyl)-2H-benzotriazole;
2-(2-hydroxy-3-alpha-cumyl-5-tert-octylphenyl)-2H-benzotriazole;
2-(2-hydroxy-5-tert-octylphenyl)-2H-benzotriazole;
3-(2H-benzotriazol-2-yl)-4-hydroxy-5-(1-methylpropyl)-benzenesulfonic acid monosodium salt;
3-tert-butyl-4-hydroxy-5-(2H-benzotriazol-2-yl)-hydrocinnamic acid and sodium salt;
12-hydroxy-3,6,9-trioxadodecyl 3-tert-butyl-4-hydroxy-5-(2H-benzotriazol-2-yl)-hydrocinnamate; octyl 3-tert-butyl-4-hydroxy-5-(2H-benzotriazol-2-yl)-hydrocinnamate;
4,6-bis(2,4-dimethylphenyl)-2-(4-(3-dodecyloxy*-2-hydroxypropoxy)-2-hydroxyphenyl)-s-triazine (*is mixture of $C_{12-14}$oxy isomers);
4,6-bis(2,4-dimethylphenyl)-2-(4-octyloxy-2-hydroxyphenyl)-s-triazine;
2,4-dihydroxybenzophenone;
2,2'-dihydroxy-4,4'-dimethoxy-5,5'-disulfobenzophenone, disodium salt;
2-hydroxy-4-octyloxybenzophenone;
2-hydroxy-4-dodecyloxybenzophenone;
2,4-dihydroxybenzophenone;
2,2',4,4'-tetrahydroxybenzophenone;
4-aminobenzoic acid;
2,3-dihydroxypropyl-4-aminobenzoic acid;
3-(4-imidazolyl)acrylic acid;
2-phenyl-5-benzimidazole sulfonic acid;
N,N,N-trimethyl-alpha-(2-oxo-3-bornylidene)-p-toluidinium methyl sulfate;
5-benzoyl-4-hydroxy-2-methoxybenzenesulfonic acid, sodium salt;
3-(4-benzoyl-3-hydroxyphenoxy)-2-hydroxy-N,N,N-trimethyl-1-propanaminium chloride;
3-[4-(2H-benzotriazol-2-yl)-3-hydroxyphenoxy]-2-hydroxy-N,N,N-trimethyl-1-propanaminium, chloride;
2-(2-hydroxy-5-methylphenyl)-2H-benzotriazole; and
2,2'-dihydroxy-4,4'-dimethoxybenzophenone (Uvinul® 3049).

For instance, suitable UV absorbers are selected from:
3-(2H-benzotriazol-2-yl)-4-hydroxy-5-(1-methylpropyl)-benzenesulfonic acid monosodium salt;
3-tert-butyl-4-hydroxy-5-(2H-benzotriazol-2-yl)-hydrocinnamic acid and sodium salt;
2-(2-hydroxy-3,5-di-tert-butylphenyl)-2H-benzotriazole;
2-(2-hydroxy-3,5-di-tert-amylphenyl)-2H-benzotriazole;
4,6-bis(2,4-dimethylphenyl)-2-(4-(3-dodecyloxy*-2-hydroxypropoxy)-2-hydroxyphenyl)-s-triazine (*is mixture of $C_{12-14}$oxy isomers);
12-hydroxy-3,6,9-trioxadodecyl 3-tert-butyl-4-hydroxy-5-(2H-benzotriazol-2-yl)-hydrocinnamate;
2,4-dihydroxybenzophenone;
2,2'-dihydroxy-4,4'-dimethoxy-5,5'-disulfobenzophenone, disodium salt;
2,2',4,4'-tetrahydroxybenzophenone;
3-(4-benzoyl-3-hydroxyphenoxy)-2-hydroxy-N,N,N-trimethyl-1-propanaminium chloride;
3-[4-(2H-benzotriazol-2-yl)-3-hydroxyphenoxy]-2-hydroxy-N,N,N-trimethyl-1-propanaminium, chloride;
5-benzoyl-4-hydroxy-2-methoxy-benzenesulfonic acid, sodium salt; and 2-(2-hydroxy-3-alpha-cumyl-5-tert-octylphenyl)-2H-benzotriazole.
Additional suitable antioxidants are for example selected from the hindered phenolic and benzofuranone stabilizers.
Suitable antioxidants are, for example, selected from the group consisting of
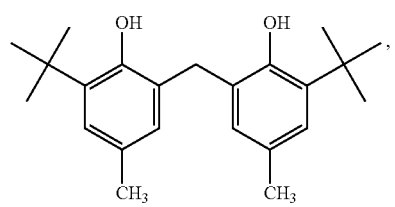
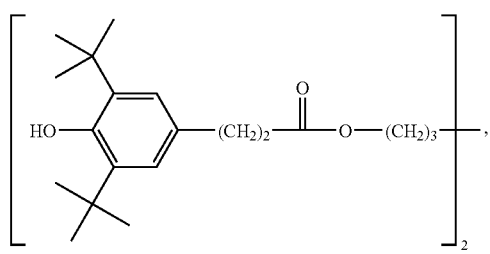
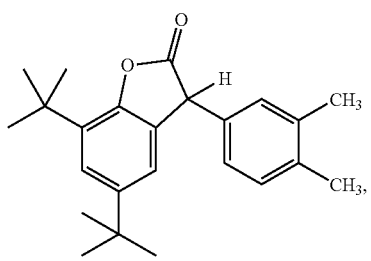
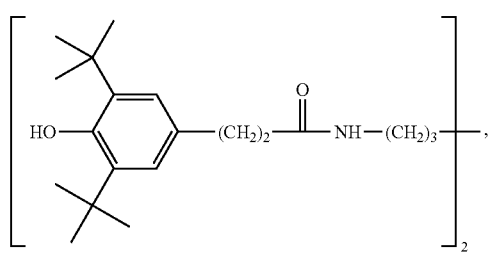
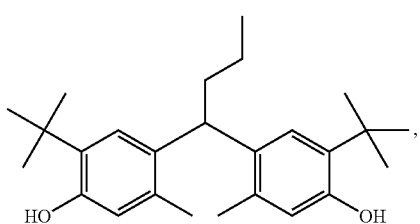
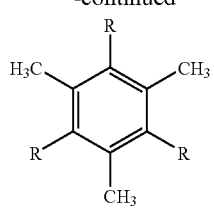
-continued
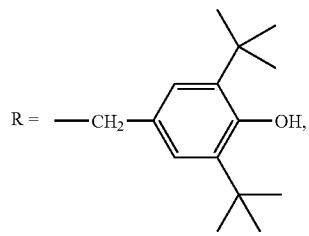
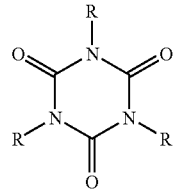
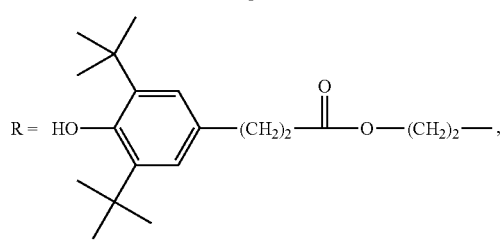
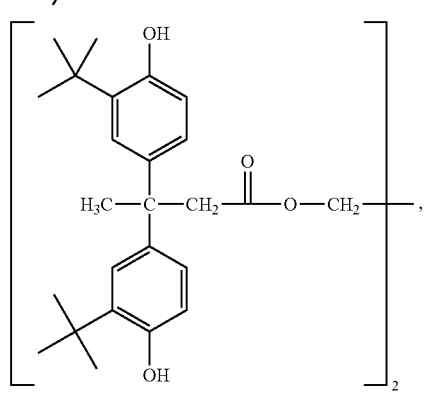
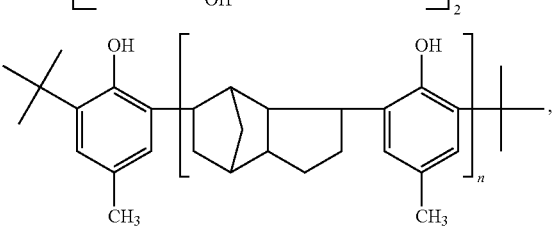
n = 1-3
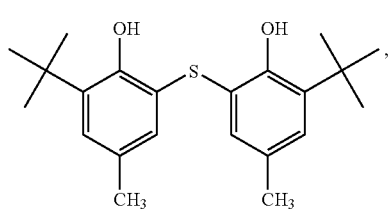

-continued
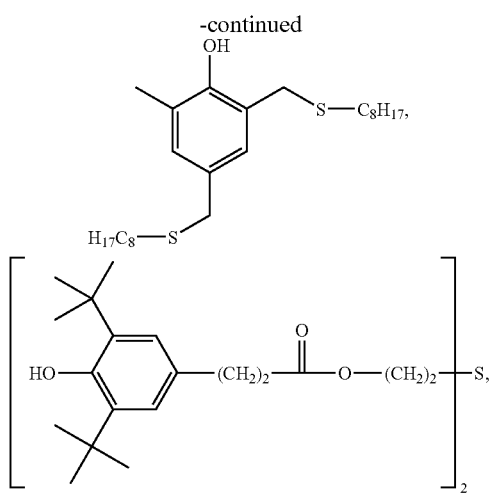
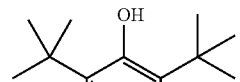
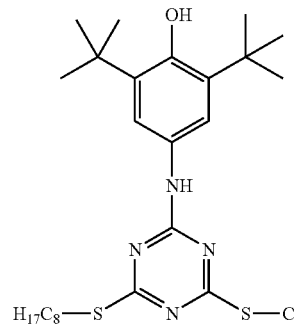
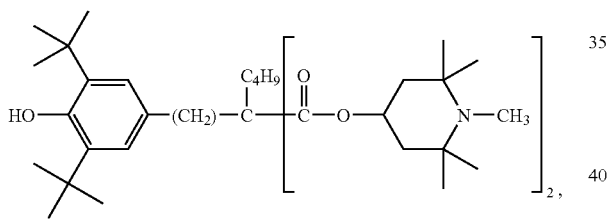
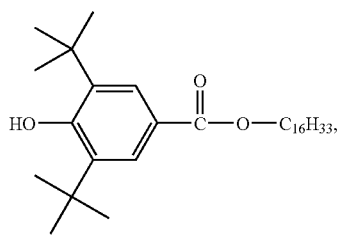
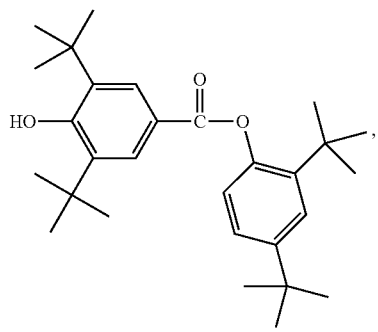
-continued
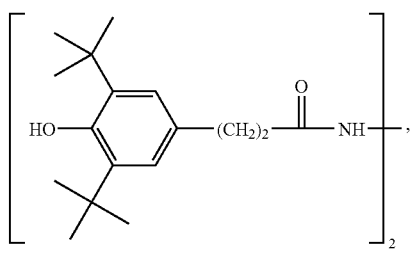
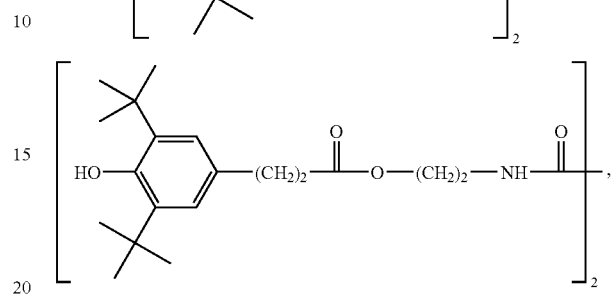
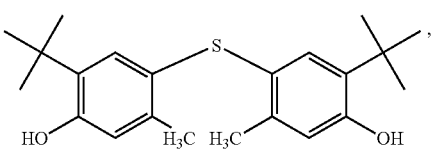
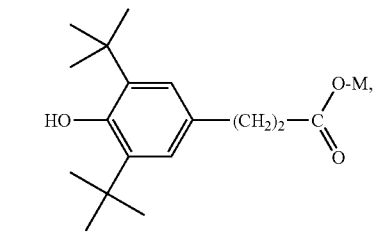
M = H, ammonium, alkali
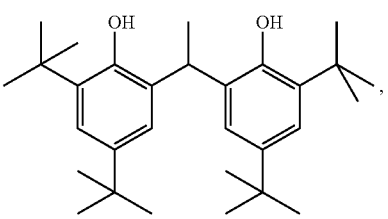
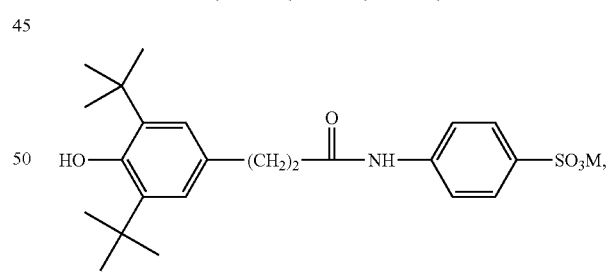
M = H, Na
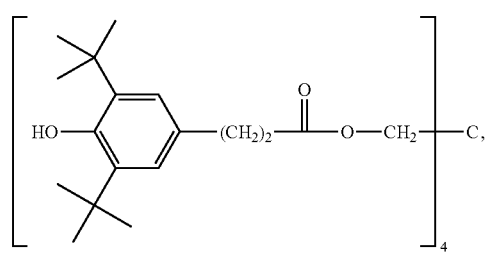

-continued

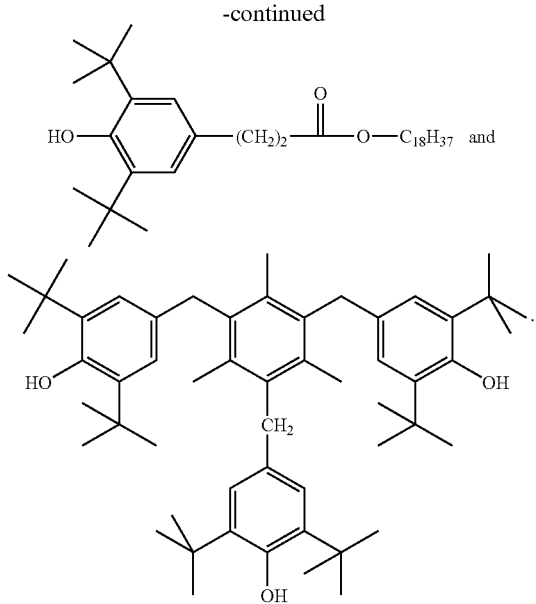

The hindered amine light stabilizers (HALS) of component (c) are for example known commercial compounds. They are for example selected from the group consisting of bis(2,2,6,6-tetramethylpiperidin-4-yl)sebacate, bis(2,2,6,6-tetramethylpiperidin-4-yl)succinate, bis(1,2,2,6,6-pentamethylpiperidin-4-yl)sebacate, n-butyl-3,5-di-tert-butyl-4-hydroxybenzylmalonic acid-bis(1,2,2,6,6-pentamethylpiperidyl)ester, the condensate of 1-hydroxyethyl-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, the condensate of N,N-bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino) ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)-pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-4-piperidyl)hexamethylenediamine and 4-cyclohexylamino-2,6-dichloro-1,3,5-triazine, the condensate of 1,2-bis(3-aminopropylamino)ethane and 2,4,6-trichloro-1,3,5-triazine and 4-butylamino-2,2,6,6-tetramethylpiperidine (CAS reg. No. [136504-96-6]); (2,2,6,6-tetramethyl-4-piperidyl)-n-dodecylsuccinimide, (1,2,2,6,6-pentamethyl-4-piperidyl)-n-dodecylsuccinimide, 2-undecyl-7,7,9,9-tetramethyl-1-oxa-3,8-diaza-4-oxo-spiro[4,5] decane, the reaction product of 7,7,9,9-tetramethyl-2-cycloundecyl-1-oxa-3,8-diaza-4-oxospiro[4,5]decane and epichlorohydrin, tetra(2,2,6,6-tetramethylpiperidin-4-yl)-butane-1,2,3,4-tetracarboxylate, tetra(1,2,2,6,6-pentamethylpiperidin-4-yl)-butane-1,2,3,4-tetracarboxylate, 2,2,4,4-tetramethyl-7-oxa-3,20-diaza-21-oxo-dispiro[5.1.11.2]-heneicosan, 8-acetyl-3-dodecyl-1,3,8-triaza-7,7,9,9-tetramethylspiro[4,5]-decane-2,4-dione,

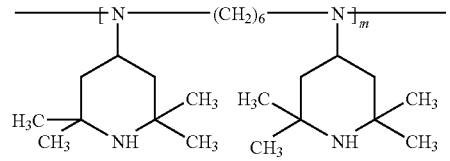

wherein m is a value from 5-50,

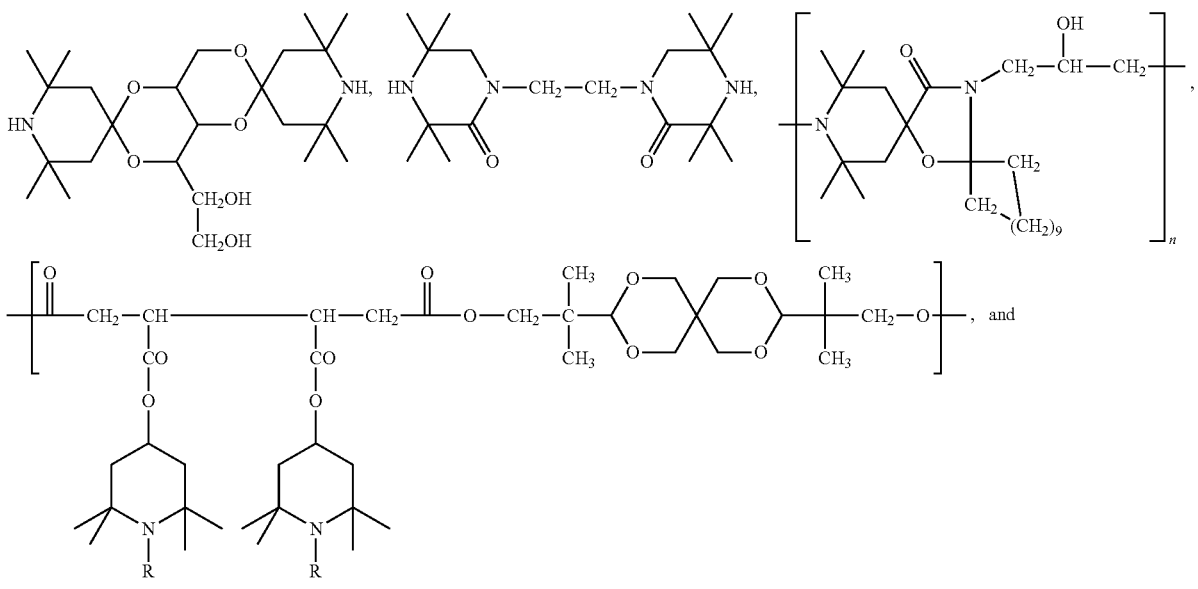

where R = H or CH$_3$

-continued

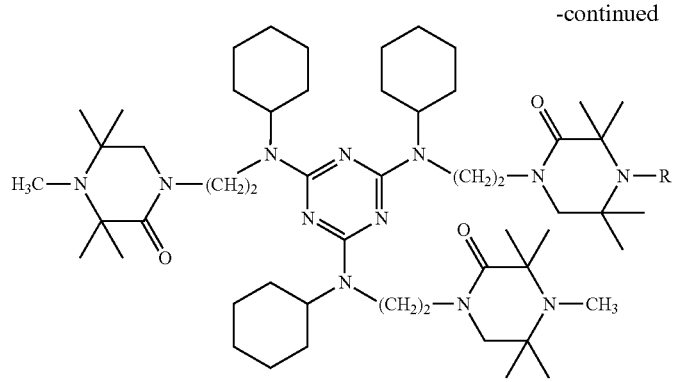

where R=H or CH$_3$

The complex formers of component (c) are for example nitrogen-containing complex formers or polyanionically-derived natural polysaccharides, for example those containing phosphate, phosphonate or methylphosphonate groups, such as chitin derivatives, e.g. sulfochitin, carboxymethylchitin, phosphochitin or chitosan derivatives, for example sulfochitosan, carboxymethylchitosan or phosphochitosan.

The complex formers of component (c) are, for example, selected from the group consisting of ethylenediaminetetracetic acid (EDTA), nitrilotriacetic acid (NTA), beta-alaninediacetic acid (EDETA) or ethylenediaminedisuccinic acid (EDDS),

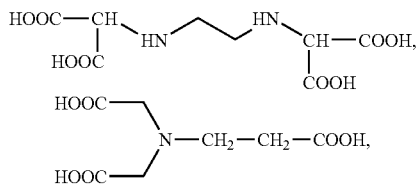

aminetrimethylenephosphoric acid (ATMP) conforming to formula

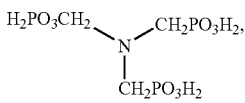

serinediacetic acid (SDA) conforming to formula

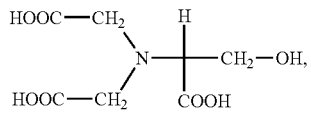

asparaginediacetic acid conforming to formula

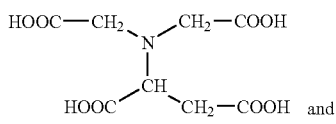

methylglycinediacetic acid (MGDA) conforming to formula

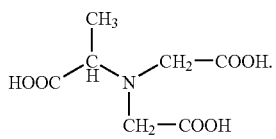

The polyorganosiloxanes of component (c) are, for example, listed in WO 2001/41719, U.S. Pat. No. 6,432,894, U.S. Pat. No. 6,383,995, US 2004/0105832 and U.S. Pat. No. 6,403,542, the US references are herein incorporated by reference.

Component (c) of the personal care compositions preferably comprise no more than about 10 weight percent of the composition; more preferably no more than about 7 weight percent of the personal care composition; even more preferably no more than about 5 weight percent; and still more preferably no more than about 3 weight percent. The component (c) of the personal care composition preferably comprise at least about 0.0001 weight percent of the personal care composition, more preferably at least about 0.01 weight percent, even more preferably at least about 0.1 weight percent, and still more preferably at least about 0.2 by weight of the composition.

The present cationic terpolymers of formula (I) are particularly suitable for personal care compositions or products, in particular for use in skin-care products, as bath and shower products, preparations containing fragrances and odoriferous substances, hair-care products, dentifrices, deodorizing and antiperspirant preparations, decorative preparations, light protection formulations and preparations containing active ingredients.

Suitable skin-care products are, in particular, body oils, body lotions, body gels, treatment creams, skin protection ointments, shaving preparations, such as shaving foams or gels, skin powders, such as baby powder, moisturising gels, moisturising sprays, revitalising body sprays, cellulite gels and peeling preparations.

Preparations containing fragrances and odoriferous substances are in particular scents, perfumes, and shaving lotions (aftershave preparations).

Suitable hair-care products are, for example, shampoos for humans and animals, in particular dogs and cats, hair conditioners, products for styling and treating hair, perming agents, hair sprays and lacquers, hair gels, hair fixatives and hair dyeing or bleaching agents.

Suitable dentifrices are in particular tooth creams, toothpastes, mouthwashes, mouth rinses, anti-plaque preparations and cleaning agents for dentures.

Suitable decorative preparations are in particular lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, vegetable extract preparations and antibacterial preparations.

The present personal care compositions or products can be in the form of creams, ointments, pastes, foams, gels, lotions, powders, make-ups, sprays, sticks or aerosols. The present cationic terpolymers of formula (I) may be present in the oil phase or in the aqueous or aqueous/alcoholic phase.

Creams are oil-in-water emulsions containing more than 50% water. The oil-containing base used therein is usually mainly fatty alcohols, for example lauryl, cetyl or stearyl alcohol, fatty acids, for example palmitic or stearic acid, liquid to solid waxes, for example isopropylmyristate or beeswax and/or hydrocarbon compounds, such as paraffin oil. Suitable emulsifiers are surfactants having primarily hydrophilic properties, such as the corresponding nonionic emulsifiers, for example fatty acid esters of polyalcohols of ethylene oxide adducts, such as polyglycerol fatty acid ester or polyoxyethylenesorbitan fatty acid ether (TWEEN trademarks); polyoxyethylene fatty alcohol ether or their esters or the corresponding ionic emulsifiers, such as the alkali metal salts of fatty alcohol sulfonates, sodium cetyl sulfate or sodium stearyl sulfate, which are usually used together with fatty alcohols, such as cetyl alcohol or stearyl alcohol. In addition, creams contain agents which reduce water loss during evaporation, for example polyalcohols, such as glycerol, sorbitol, propylene glycol, and/or polyethylene glycols.

Ointments are water-in-oil emulsions which contain up to 70%, for instance not more than 20 to 50%, of water or of an aqueous phase. The oil-containing phase contains predominantly hydrocarbons, such as paraffin oil and/or solid paraffin which for instance contains hydroxy compounds, for example fatty alcohol or their esters, such as cetyl alcohol or wool wax for improving the water absorption. Emulsifiers are corresponding lipophilic substances, such as sorbitan fatty acid ester. In addition, the ointments contain moisturisers such as polyalcohols, for example glycerol, propylene glycol, sorbitol and/or polyethylene glycol as well as preservatives.

Rich creams are anhydrous formulations and are produced on the basis of hydrocarbon compounds, such as paraffin, natural or partially synthetic fats, for example coconut fatty acid triglycerides or, for instance, hardened oils and glycerol partial fatty acid esters.

Pastes are creams and ointments containing powdered ingredients which absorb secretions, for example metal oxides, such as titanium dioxide or zinc oxide, and also tallow and/or aluminium silicates which bind the moisture or the absorbed secretion.

Foams are liquid oil-in-water emulsions in aerosol form. Hydrocarbon compounds are used, inter alia, for the oil-containing phase, for example paraffin oil, fatty alcohols, such as cetyl alcohol, fatty acid esters, such as isopropylmyristate and/or waxes. Suitable emulsifiers are, inter alia, mixtures of emulsifiers having predominantly hydrophilic properties, for example polyoxyethylenesorbitan fatty acid ester, and also emulsifiers having predominantly lipophilic properties, for example sorbitan fatty acid ester. Commercially available additives are usually additionally employed, for example preservatives.

Gels are, in particular, aqueous solutions or suspensions of active substances in which gel formers are dispersed or swelled, in particular cellulose ethers, such as methyl cellulose, hydroxyethyl cellulose, carboxymethyl cellulose or vegetable hydrocolloids, for example sodium alginate, tragacanth or gum Arabic and polyacrylate thickener systems. The gels for example additionally contain polyalcohols, such as propylene glycol or glycerol as moisturisers and wetting agents, such as polyoxyethylenesobitan fatty acid ester. The gels furthermore contain commercially available preservatives, such as benzyl alcohol, phenethyl alcohol, phenoxyethanol and the like.

The following is a partial list of examples of personal care products of this invention and their ingredients:

| Body care product | Ingredients |
|---|---|
| moisturizing cream | vegetable oil, emulsifier, thickener, perfume, water, antioxidant, UV absorbers, cationic terpolymers of the instant invention |
| shampoo | surfactant, emulsifier, preservatives, perfume, antioxidant, UV absorbers, cationic terpolymers of the instant invention |
| toothpaste | cleaning agent, thickener, sweetener, flavor, colorant, antioxidant, water, UV absorbers, cationic terpolymers of the instant invention |
| lip-care stick | vegetable oil, wax, $TiO_2$, antioxidant, UV absorbers, cationic terpolymers of the instant invention |

The present personal care compositions may further comprise dyes, pigments or mixtures thereof.

Accordingly, the present invention further pertains to a personal care composition comprising (a) an effective amount of at least one cationic terpolymer of formula (I)

wherein j, t, u, v, w, x, and z represent the percentage by weight that each repeating unit or derived monomer is contained within the terpolymer;

* is a terminal group, for example a catalyst residue;

j, t, u, v, w, x, and z add up to total 100 percent and are based on weight of the terpolymer;

j, u and x are independently from 0.0001 to 39.9997% based on weight of the terpolymer;

j+u+x is less than or equal to 39.9999% percent based on the weight of the terpolymer;

w is from about 0.0001% to about 20% by weight of the terpolymer;

t is from about 0% to about 20% by weight of the terpolymer;

z and v are independently from about 0.0001 to about 60% based on weight of the terpolymer;

z+v is equal to or greater than 60 percent based on the weight of the terpolymer;

E is derived from a difunctional siloxane monomer of formula (II)

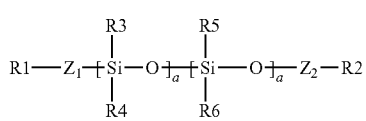

(II)

R1 and R2 independently are a polymerizable function from the group of the vinylically unsaturated compounds which is suitable for the synthesis of polymeric structures by a free-radical route or by condensation and represents vinyl, allyl, methallyl, methylvinyl, acryloyl (CH2=CH—CO—), methacryloyl (CH2=C[CH3]—CO—), crotonyl, senecionyl, itaconyl, maleyl, fumaryl, epoxy or styryl radicals;

Z1 is a direct bond or a bridging group selected from the group consisting of —O—, —((C1-C50)alkylene), —((C6-C30)arylene)-, —((C5-C8)cycloalkylene)-, —((C1-C50)alkenylene)-, -(polypropylene oxide)n-, -(polyethylene oxide)o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;

Z2 is a direct bond or a bridging group selected from the group consisting of —((C1-C50)alkylene), —((C6-C30)arylene)-, —((C5-C8)cycloalkylene)-, —((C1-C50)alkenylene)-, -(polypropylene oxide)n-, -(polyethylene oxide)o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;

R3, R4, R5, and R6 are independently straight or branched alkyl chain of 1 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl groups of 1 to 4 carbon atoms; or said alkyl substituted by one or more —OH, —OCO—$R_{10}$, —$OR_{10}$, or —$NH_2$ groups or mixtures thereof; or said alkyl interrupted by one or more —O—, —NH— or —$NR_{10}$— groups or mixtures thereof and which can be unsubstituted or substituted by one or more —OH, —$OR_{10}$ or —$NH_2$ groups or mixtures thereof; or $OR_{11}$;

$R_{10}$ is straight or branched chain alkyl of 1 to 24 carbon atoms or phenyl or benzyl;

$R_{11}$ is straight or branched chain alkyl of 1 to 24 carbon atoms or phenyl or benzyl; or said alkyl substituted by one or more —OH, —OCO—$R_{10}$, —$OR_{10}$, or —$NH_2$ groups or mixtures thereof; or said alkyl interrupted by one or more —O—, —NH— or —$NR_{10}$— groups or mixtures thereof and which can be unsubstituted or substituted by one or more —OH, —$OR_{10}$ or —$NH_2$ groups or mixtures thereof;

a and b represent stoichiometric coefficients which amount independently of one another to from 1 to 5000; or E is derived from a difunctional polypropylene glycol or polyethylene glycol monomer of formula (VI);

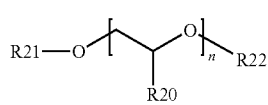

(VI)

R20 is hydrogen or methyl; R21 and R22 are independently vinyl, allyl, methallyl, methylvinyl, acryloyl (CH2=CH—CO—), methacryloyl (CH2=C[CH3]—CO—), crotonyl, senecionyl, itaconyl, maleyl, fumaryl, epoxy or styryl radicals;

Fg is the residue from at least one functional reactant grafted onto a cationic amino base polymer;

G and T are independently derived from a monomer selected from the group consisting of diallyldimethyl ammonium chloride (DADMAC), diallyidimethyl ammonium bromide, diallyidimethyl ammonium sulfate, diallyldimethyl ammonium phosphates, dimethallyldimethyl ammonium chloride, diethylallyl dimethyl ammonium chloride, diallyl di(beta-hydroxyethyl) ammonium chloride, and diallyl di(beta-ethoxyethyl) ammonium chloride;

M, D and A are independently derived from a monomer of formula (III)

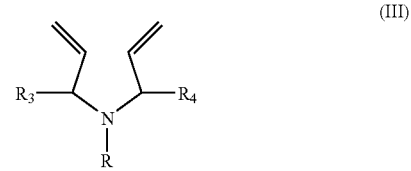

(III)

where R, $R_3$ and $R_4$ are, independently of each other, hydrogen or $C_1$-$C_4$alkyl;

(b) a cosmetically acceptable adjuvant, and (d) a dye or a pigment or mixtures thereof.

Dyes of component (d) according to the present invention are for example:
  disperse dyes which may be solubilzed in solvents like direct hair dyes of the HC type, for example HC Red No. 3, HC Blue No. 2 and all other hair dyes listed in International Cosmetic Ingredient Dictionary and Handbook, $7^{th}$ edition 19997) or the dispersion dyes listed in Color Index International or Society of Dyers and Colourists;
  color varnishes (insoluble salts of soluble dyes, like many Ca-, Ba- or Al-salts of anionic dyes);
  soluble anionic or cationic dyes, like acid dyes (anionic), basic dyes (cationic), direct dyes, reactive dyes or solvent dyes.

Generally, for the coloration of personal care compositions, all substances are suitable which have an absorption in the visible light of electromagnetic radiation (wavelength of ca. 4000 to 700 nm). The absorption is often caused by the following chromophores:

Azo-(mono-, di, tris-, or poly-)stilbene-, carotenoide-, diarylmethan-, triarylmethan-, xanthen-, acridin-, quinoline, methin-(also polymethin-), thiazol-, indamin-, indophenol-, azin-, oxazin, thiazin-, anthraquinone-, indigoid-, phtalocyanine- and further synthetic, natural and/or inorganic chromophores.

According to the instant invention, pigments of component (d) include inorganic pigments, metal oxides and hydroxides, mica, organic pigments, pearlescent pigments, mineral silicates, porous materials, carbons, interference pigments, and the like.

Examples of the inorganic pigments of component (d) capable of being utilized according to the present invention are ultramarine blue, ultramarine violet, Prussian blue, manganese violet, titanium-coated mica, bismuth oxychloride, iron oxides, iron hydroxide, titanium dioxide, titanium lower oxides, chromium hydroxide and oxides, and carbon based pigments (e.g. Carbon Black). Of these inorganic pigments, ultramarine blue and Prussian blue are particular advantageous.

According to the instant invention, the range of useful organic pigments of component (d) may comprise monoazo, disazo, naphthol, dioxazone, azomethin, azocondensation, metal complex, nitro, perinone, quinoline, anthraquinone, benzimidozolone, isoindoline, isoindolinone, triarylmethane, quinacridone, hydroxyanthraquinone, aminoanthraquinone, anthrapyrimidine, indanthrone, flavanthrone, pyranthrone, anthantrone, isoviolanthrone, diketopyrrolopyrrole, carbazole, indigo or thiolndigo pigments.

According to the instant invention, examples of the organic pigments of component (d) are C.I. 15850, C.I. 15850:1, C.I. 15585:1, C.I. 15630, C.I. 15880:1, C.I. 73360, C.I. 12085, C.I. 15865:2, C.I. 12075, C.I. 21110, C.I. 21095, and C.I. 11680, C.I. 74160 and zirconium, barium, or aluminum lakes of C.I. 45430, C.I. 45410, C.I. 45100, C.I. 17200, C.I. 45380, C.I. 45190, C.I. 14700, C.I. 15510, C.I. 19140, C.I. 15985, C.I. 45350, C.I. 47005, C.I. 42053, C.I. 42090.

C.I. means Colour Index as compiled by the by The Society of Dyers and Colourists and The American Association of Textile Chemists and Colourists.

According to the instant invention, mixtures of the organic pigments of component (d) may be used.

According to the instant invention, mixtures of the inorganic and organic pigments of component (d) may be used.

According to the instant invention, mixtures of dyes and organic and/or inorganic pigments of component (d) may be used.

Component (d) of the personal care compositions preferably comprise no more than about 10 weight percent of the composition; more preferably no more than about 7 weight percent of the personal care composition; even more preferably no more than about 5 weight percent; and still more preferably no more than about 3 weight percent. The component (d) of the personal care composition preferably comprise at least about 0.0001 weight percent of the personal care composition, more preferably at least about 0.01 weight percent, even more preferably at least about 0.1 weight percent, and still more preferably at least about 0.2 by weight of the composition.

Personal care compositions according to the invention may be generally applied to the skin and/or hair of humans and/or animals.

The present invention also pertains to a cationic terpolymer comprising
(a) an effective amount of at least one cationic terpolymer of formula (I)

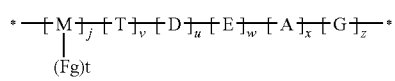

(I)

wherein
j, t, u, v, w, x, and z represent the percentage by weight that each repeating unit or derived monomer is contained within the terpolymer;
* is a terminal group, for example a catalyst residue;
j, t, u, v, w, x, and z add up to total 100 percent and are based on weight of the terpolymer;
j, u and x are independently from 0.0001 to 39.9997% based on weight of the terpolymer;
j+u+x is less than or equal to 39.9999% percent based on the weight of the terpolymer;
w is from about 0.0001% to about 20% by weight of the terpolymer;
t is from about 0% to about 20% by weight of the terpolymer;
z and v are independently from about 0.0001 to about 60% based on weight of the terpolymer;
z+v is equal to or greater than 60 percent based on the weight of the terpolymer;
E is derived from a difunctional siloxane monomer of formula (II)

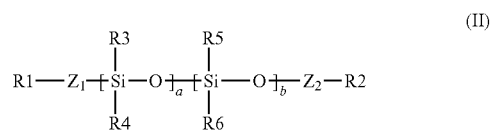

(II)

R1 and R2 independently are a polymerizable function from the group of the vinylically unsaturated compounds which is suitable for the synthesis of polymeric structures by a free-radical route or by condensation and represents vinyl, allyl, methallyl, methylvinyl, acryloyl (CH2=CH—CO—), methacryloyl (CH2=C[CH3]—CO—), crotonyl, senecionyl, itaconyl, maleyl, fumaryl, epoxy or styryl radicals;

Z1 is a direct bond or a bridging group selected from the group consisting of —O—, —((C1-C50)alkylene), —((C6-C30)arylene)-, —((C5-C8)cycloalkylene)-, —((C1-C50)alkenylene)-, -(polypropylene oxide)n-, -(polyethylene oxide)o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;

Z2 is a direct bond or a bridging group selected from the group consisting of —((C1-C50)alkylene), —((C6-C30)arylene)-, —((C5-C8)cycloalkylene)-, —((C1-C50)alkenylene)-, -(polypropylene oxide)n-, -(polyethylene oxide)o-, -(polypropylene-oxide)n(polyethylene oxide)o, where n and o independently of one another denote numbers from 0 to 200 and the distribution of the EO/PO units can be random or in the form of blocks, —((C1-C10)alkyl)-(Si(OCH3)2)- and —(Si(OCH3)2)-;

R3, R4, R5, and R6 are independently straight or branched alkyl chain of 1 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl groups of 1 to 4 carbon atoms; or said alkyl substituted by one or more —OH, —OCO—$R_{10}$, —O$R_{10}$, or —NH2 groups or mixtures thereof; or said alkyl interrupted by one or more —O—, —NH— or —N$R_{10}$— groups or mixtures thereof and which can be unsubstituted or substituted by one or more —OH, —O$R_{10}$ or —NH2 groups or mixtures thereof; or O$R_{11}$;

$R_{10}$ is straight or branched chain alkyl of 1 to 24 carbon atoms or phenyl or benzyl;

$R_{11}$ is straight or branched chain alkyl of 1 to 24 carbon atoms or phenyl or benzyl; or said alkyl substituted by one or more —OH, —OCO—$R_{10}$, —O$R_{10}$, or —NH2 groups or mixtures thereof; or said alkyl interrupted by one or more —O—, —NH— or —N$R_{10}$— groups or mixtures thereof and which can be unsubstituted or substituted by one or more —OH, —O$R_{10}$ or —NH2 groups or mixtures thereof;

a and b represent stoichiometric coefficients which amount independently of one another to from 1 to 5000; or E is derived from a difunctional polypropylene glycol or polyethylene glycol monomer of formula (VI);

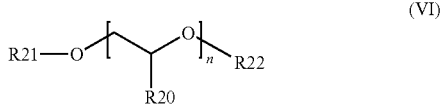

R20 is hydrogen or methyl; R21 and R22 are independently vinyl, allyl, methallyl, methylvinyl, acryloyl (CH2=CH—CO—), methacryloyl (CH2=C[CH3]—CO—), crotonyl, senecionyl, itaconyl, maleyl, fumaryl, epoxy or styryl radicals;

Fg is the residue from at least one functional reactant grafted onto a cationic amino base polymer;

G and T are independently derived from a monomer selected from the group consisting of diallyldimethyl ammonium chloride (DADMAC), diallyldimethyl ammonium bromide, diallyldimethyl ammonium sulfate, diallyldimethyl ammonium phosphates, dimethallyidimethyl ammonium chloride, diethylallyl dimethyl ammonium chloride, diallyl di(beta-hydroxyethyl) ammonium chloride, and diallyl di(beta-ethoxyethyl) ammonium chloride;

M, D and A are independently derived from a monomer of formula (III)

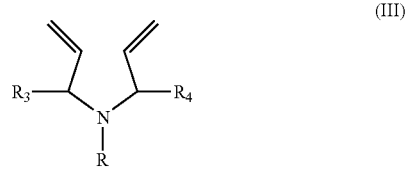

where R, $R_3$ and $R_4$ are, independently of each other, hydrogen or $C_1$-$C_4$ alkyl.

Another embodiment of the instant invention is a method for the conditioning treatment of keratin-containing fibers, wherein said method comprises contacting said fibers with an effective amount of a personal care composition or formulation comprising an effective amount of one or more cationic terpolymers of formula (I).

Another embodiment of the instant invention is a method for the conditioning treatment of mammalian keratin-containing fibers, wherein said method comprises contacting said fibers with an effective amount of a personal care composition or formulation comprising one or more cationic terpolymers of formula (I).

Another embodiment of the instant invention is a method for the treatment of mammalian skin, wherein said method comprises contacting said skin with an effective amount of a personal care composition or formulation comprising one or more cationic terpolymers of formula (I).

Personal care compositions according to the invention may be contained in a wide variety of personal care preparations. Especially the following preparations, for example, come into consideration:

shaving preparations, e.g. shaving soap, foaming shaving creams, non-foaming shaving creams, foams and gels, preshave preparations for dry shaving, aftershaves or aftershave lotions;

skin-care preparations, e.g. skin emulsions, multi-emulsions or skin oils, body powders, hot-oil treatments, and exfoliating masques;

cosmetic personal care preparations, e.g. facial make-up in the form of lipsticks, eye shadow, eye liners, liquid make-up, day creams or powders, facial lotions, foundations, creams and powders (loose or pressed), hair removal systems;

light-protective preparations, such as sun tan lotions, creams and oils, sun blocks, pretanning preparations and sunless tanning preparations;

manicure preparations, e.g. nail polishes, nail enamels, enamel removers, nail treatments deodorants, e.g. deodorant sprays, pump-action sprays, deodorant gels, sticks or roll-ons;

antiperspirants, such as antiperspirant sticks, creams or roll-ons; and solid/liquid personal cleaning products, such as soap, cleansers, shampoo, conditioners, hair treatments.

Another embodiment of the instant invention is a personal care composition comprising said dye-polymer complexes which is formulated as a water-in-oil or oil-in-water emulsion, as an alcoholic or alcohol-containing formulation, as a vesicular dispersion of an ionic or non-ionic amphiphilic lipid, as a gel, or a solid stick as an aqueous or non-aqueous system.

Another embodiment of the instant invention is a personal care composition wherein the personal care or cosmetic composition additionally comprises a blend of pigment particles that are individually provided in a single matrix material.

The personal care compositions of the present invention may contain one or more additional skin care or hair care components. In a preferred embodiment, where the composition is to be in contact with human or animal keratinous tissue, the additional components should be suitable for application to keratinous tissue, that is, when incorporated into the composition they are suitable for use in contact with human or animal keratinous tissue without undue toxicity, incompatibility, instability, allergic response, and the like within the scope of sound medical judgment.

The instant compositions may further comprise, cosmetically acceptable ingredients and adjuvants of component (b) selected, in particular but not limited to, from among fatty substances, organic solvents, oil structurants, surfactants, emulsifiers, thickeners, organic cationic deposition polymers, demulcents, opacifiers, additional colorants, effect pigments, additional stabilizers, emollients, antifoaming agents, moisturizing agents, antioxidants, vitamins, peptides, amino acids, botanical extracts, particulates, perfumes, preservatives, polymers, fillers, sequestrants, propellants, alkalinizing or acidifying agents or other optional ingredients customarily formulated into cosmetics or other personal care compositions according to the invention.

The fatty substances may be an oil or a wax or mixtures thereof, and they also comprise fatty acids, fatty alcohols and esters of fatty acids. The oils may be selected from among animal, vegetable, mineral or synthetic oils and, in particular, from among liquid paraffin, paraffin oil, silicone oils, volatile or otherwise, isoparaffins, polyolefins, fluorinated or perfluorinated oils. Likewise, the waxes may be animal, fossil, vegetable, mineral or synthetic waxes which are also known per se.

Exemplary organic solvents may include the lower alcohols and polyols.

Of course, one skilled in this art will take care to select this or these optional additional compounds and/or their quantities such that the advantageous properties, in particular the resistance to water, the stability, which are intrinsically associated with the sunscreen compositions in accordance with the invention are not, or not substantially, altered by the addition(s) envisaged.

The CTFA Cosmetic Ingredient Handbook, Second Edition (1992) describes a wide variety of non-limiting cosmetic and pharmaceutical ingredients commonly used in the personal care industry, which are suitable for use in the personal care compositions of the present invention.

The present invention may optionally comprise an oil structurant. The structurant can provide the dispersed phase with the correct rheological properties. This can aid in providing effective deposition and retention to the skin, the structured oil or oil phase should have a viscosity in the range of 100 to about 200,000 poise measured at 1 Sec-1, preferably 200 to about 100,000 poise, and most preferably 200 to about 50,000 poise. The amount of structurant required to produce this viscosity will vary depending on the oil and the structurant, but in general, the structurant will preferably be less than 75 weight percent of the dispersed oil phase, more preferably less than 50 weight percent, and still more preferably less than 35 weight percent of the dispersed oil phase.

The structurant can be either an organic or inorganic structurant. Examples of organic thickeners suitable for the invention are solid fatty acid esters, natural or modified fats, fatty acid, fatty amine, fatty alcohol, natural and synthetic waxes, and petrolatum, and the block copolymers sold under the name KRATON by Shell. Inorganic structuring agents include hydrophobically modified silica or hydrophobically modified clay. Nonlimiting examples of inorganic structurants are BENTONE 27V, BENTONE 38V or BENTONE GEL MIO V from Rheox; and CAB-O-SIL TS720 or CAB-O-SIL M5 from Cabot Corporation.

Structurants meeting the above requirements with the selected skin compatible oil can form 3-dimensional network to build up the viscosity of the selected oils. It has been found that such structured oil phases, i.e., built with the 3-dimensional network, are extremely desirable for use as wet-skin treatment compositions used in bathing. These structured oils can deposit and be retained very effectively on wet skin and retained after rinsing and drying to provide long-lasting after wash skin benefit without causing a too oily/greasy wet and dry feel. It is believed that the highly desirable in-use and after-use properties of such structured oils are due to their shear thinning rheological properties and the weak structure of the network. Due to its high low-shear viscosity, the 3-dimensional network structured oil can stick and retain well on the skin during application of the skin conditioner. After being deposited on the skin, the network yields easily during rubbing due to the weak structuring of the crystal network and its lower high-shear viscosity.

A wide variety of surfactants can be useful herein, both for emulsification of the dispersed phase as well as to provide acceptable spreading and in use properties for non-lathering systems. For cleansing applications, the surfactant phase also serves to clean the skin and provide an acceptable amount of lather for the user. The composition preferably contains no more than about 50 weight percent of a surfactant, more preferably no more than about 30 weight percent, still more preferably no more than about 15 weight percent, and even more preferably no more than about 5 weight percent of a surfactant. The composition preferably contains at least about 5 weight percent of a surfactant, more preferably at least about 3 weight percent, still more preferably at least about 1 weight percent, and even more preferably at least about 0.1 weight percent of a surfactant. For cleansing applications the personal care compositions preferably produces a Total Lather Volume of at least 300 ml, more preferably greater than 600 ml as described in the Lathering Volume Test. The personal care compositions preferably produces a Flash Lather Volume of at least 100 ml, preferably greater than 200 ml, more preferably greater than 300 ml as described in the Lathering Volume Test.

Preferable surfactants useful in the personal care compositions of the instant invention include those selected from the group consisting of anionic surfactants, nonionic surfactants, amphoteric surfactants, non-lathering surfactants, emulsifiers and mixtures thereof. Non-limiting examples of surfactants useful in the compositions of the present invention are disclosed in U.S. Pat. No. 6,280,757, to McAtee et al., issued Aug. 28, 2001, herein incorporated by reference.

Non-limiting examples of anionic surfactants useful in the personal care compositions of the present invention are disclosed in McCutcheon's, Detergents and Emulsifiers, North American edition (1986), published by Allured Publishing Corporation; McCutcheon's, Functional Materials, North American Edition (1992); and U.S. Pat. No. 3,929,678, to Laughlin et al., issued Dec. 30, 1975, herein incorporated by reference.

A wide variety of anionic surfactants are useful herein. Non-limiting examples of anionic surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred.

Other anionic materials useful herein are fatty acid soaps (i.e., alkali metal salts, e.g., sodium or potassium salts) typically having from a fatty acid having about 8 to about 24 carbon atoms, preferably from about 10 to about 20 carbon atoms. These fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps and their preparation are described in detail in U.S. Pat. No. 4,557,853, herein incorporated by reference.

Other anionic materials include phosphates such as monoalkyl, dialkyl, and trialkylphosphate salts. Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein are ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

Non-limiting examples of nonionic surfactants for use in the personal care compositions of the present invention are disclosed in McCutcheon's, Detergents and Emulsifiers, North American edition (1986), published by Allured Publishing Corporation; and McCutcheon's, Functional Materials, North American Edition (1992), herein incorporated by reference.

Nonionic surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Non-limiting examples of preferred nonionic surfactants for use herein are those selected from the group consisting of C8-C14 glucose amides, C8-C14 alkyl polyglucosides, sucrose cocoate, sucrose laurate, lauramine oxide, cocoamine oxide and mixtures thereof.

The term "amphoteric surfactant," as used herein, is also intended to encompass zwitterionic surfactants, which are well known to formulators skilled in the art as a subset of amphoteric surfactants.

A wide variety of amphoteric lathering surfactants can be used in the personal care compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, Detergents and Emulsifiers, North American edition (1986), published by Allured Publishing Corporation; and McCutcheon's, Functional Materials, North American Edition (1992), herein incorporated by reference.

Non-limiting examples zwitterionic surfactants are those selected from the group consisting of betaines, sultaines, hydroxysultaines, alkyliminoacetates, iminodialkanoates, aminoalkanoates, and mixtures thereof.

Preferred surfactants for use herein are the following, wherein the anionic surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isetlionate, sodium cetyl sulfate, sodium lauroyl lactylate, triethanolamine lauroyl lactylate, and mixtures thereof, wherein the non-ionic surfactant is selected from the group consisting of lauramine oxide, cocoamine oxide, decyl polyglucose, lauryl polyglucose, sucrose cocoate, C12-14 glucosamides, sucrose laurate, and mixtures thereof; and wherein the amphoteric surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

A wide variety of non-lathering surfactants are useful herein. The personal care compositions of the present invention can comprise a sufficient amount of one or more non-lathering surfactants to emulsify the dispersed phase to yield an appropriate particle size and good application properties on wet skin.

Nonlimiting examples of these non-lathering compositions are: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

In addition, there are several commercial emulsifier mixtures that are useful in some embodiments of the personal care compositions according to the present invention. Examples include PROLIPID 141 (glyceryl stearate, behenyl alcohol, palmitic acid, stearic acid, lecithin, lauryl alcohol, myristyl alcohol and cetyl alcohol) and 151 (Glyceryl stearate, cetearyl alcohol, stearic acid, 1-propanamium, 3-amino-N-(2-(hydroxyethyl-)-N—N-Dimethyl,N—C(16-18) Acyl Derivatives, Chlorides) from ISP; POLAWAX NF (Emulsifying wax NF), INCROQUAT BEHENYL TMS (behentrimonium sulfate and cetearyl alcohol) from Croda; and EMULLIUM DELTA (cetyl alcohol, glyceryl stearate, PEG-75 stearate, ceteth-20 and steareth-20) from Gattefosse.

The personal care compositions of the present invention, in some embodiments, may further include one or more thickening/aqueous phase stability agents. Because different stability agents thicken with different efficiencies, it is difficult to provide an accurate compositional range, however, when present, the composition preferably comprises no more than about 20 weight percent, more preferably no more than about 10 weight percent, more preferably no more than about 8 weight percent, and still more preferably no more than about 7 weight percent of the personal care composition. When present, the thickening/aqueous phase stability agent preferably comprises at least about 0.01 weight percent, more preferably at least about 0.05 weight percent, and still more preferably at least about 0.1 weight percent of the personal care composition. A better method of describing the stability agent is to say that it must build viscosity in the product. This can be measured using the Stability Agent Viscosity Test; preferably, the stability agent produces a viscosity in this test of at least 1000 cps, more preferably at least 1500 cps, and still more preferably at least 2000 cps.

Nonlimiting examples of thickening agents useful herein include carboxylic acid polymers such as the carbomers (such as those commercially available under the trade name CARBOPOL® 900 series from B.F. Goodrich; e.g., CARBOPOL® 954). Other suitable carboxylic acid polymeric agents include copolymers of C10-30 alkyl acrylates with one or more monomers of acrylic acid, methacrylic acid, or one of their short chain (i.e., C1-4 alcohol) esters, wherein the cross linking agent is an allyl ether of sucrose or pentaerytritol. These copolymers are known as acrylates/C10-30 alkyl acrylate crosspolymers and are commercially available as CARBOPOL® 1342, CARBOPOL® (1382, PEMULEN TR-1, and PEMULEN TR-2, from B.F. Goodrich.

Other nonlimiting examples of thickening agents include crosslinked polyacrylate polymers including both cationic and nonionic polymers.

Still other nonlimiting examples of thickening agents include the polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Trade name SEPIGEL 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multi-block copolymers include HYPAN SR150H, SS500V, SS500W, SSSA100H, from Lipo Chemicals, Inc., (Patterson, N.J.).

Another nonlimiting class of thickening agents useful herein is the polysaccharides. Nonlimiting examples of polysaccharide gelling agents include those selected from cellulose, and cellulose derivatives. Preferred among the alkyl hydroxyalkyl cellulose ethers is the material given the CTFA designation cetyl hydroxyethylcellulose, which is the ether of cetyl alcohol and hydroxyethylcellulose, sold under the trade name NATROSEL® CS PLUS from Aqualon Corporation (Wilmington, Del.). Other useful polysaccharides include scleroglucans which are a linear chain of (1-3) linked glucose units with a (1-6) linked glucose every three units, a commercially available example of which is CLEAROGEL™ CS 11 from Michel Mercier Products Inc. (Mountainside, N.J.).

Another nonlimiting class of thickening agents useful herein is the gums. Nonlimiting examples of gums useful herein include hectorite, hydrated silica, xantham gum, cellulose gums, guar gum, biosaccharide gums and mixtures thereof.

Yet another nonlimiting class of thickening agents useful herein is the modified starches. Acrylate modified starches such as WATERLOCK® from Grain Processing Corporation may be used. Hydroxypropyl starch phosphate, tradename STRUCTURE XL from National Starch is another example of a useful modified starch, and other useful examples include ARISTOFLEX HMB (Ammonium Acrylodimethyltaruate/ Beheneth-25 Methacrylate Crosspolymer) from Clariant and cationic stabylens.

The personal care compositions according to the present invention may also contain organic cationic deposition polymers. Concentrations of the cationic deposition polymers preferably range from about 0.025% to about 10%, more preferably from about 0.05% to about 2%, even more preferably from about 0.1% to about 1%, by weight of the personal care composition.

Suitable cationic deposition polymers for use in the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal care composition. The average molecular weight of the cationic deposition polymer is between about 5,000 to about 10 million, preferably at least about 100,000, more preferably at least about 200,000, but preferably not more than about 2 million, more preferably not more than about 1.5 million. The polymers also have a cationic charge density ranging from about 0.2 meq/gm to about 5 meq/gm, preferably at least about 0.4 meq/gm, more preferably at least about 0.6 meq/gm., at the pH of intended use of the personal care composition, which pH will generally range from about pH 4 to about pH 9, preferably between about pH 5 and about pH 8. Nonlimiting examples of cationic deposition polymers for use in the personal care compositions include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their POLYMER KG, JR and LR series of polymers with the most preferred being KG-30M.

Other suitable cationic deposition polymers include cationic guar gum derivatives, such as guar hydroxypropyltrimonium chloride, specific examples of which include the Jaguar series (preferably JAGUAR C-17) commercially available from Rhodia Inc., and N-HANCE polymer series commercially available from Aqualon.

Other suitable cationic deposition polymers include synthetic cationic polymers. The cationic polymers suitable for use in the personal cleansing composition herein are water soluble or dispersible, non cross linked, cationic polymers having a cationic charge density of from about 4 meq/gm to about 7 meq/gm, preferably from about 4 meq/gm to about 6 meq/gm, more preferably from about 4.2 meq/gm to about 5.5 meq/gm. The select polymers also must have an average molecular weight of from about 1,000 to about 1 million, preferably from about 10,000 to about 500,000, more preferably from about 75,000 to about 250,000.

A non limiting example of a commercially available synthetic cationic polymer for use in the cleansing compositions is polymethyacrylamidopropyl trimonium chloride, available under the trade name POLYCARE 133, from Rhodia, Cranberry, N.J., U.S.A.

Other non limiting examples of optional ingredients include benefit agents that are selected from the group consisting of vitamins and derivatives thereof (e.g., ascorbic acid, vitamin E, tocopheryl acetate, and the like); sunscreens; thickening agents (e.g., polyol alkoxy ester, available as CROTHIX from Croda); preservatives for maintaining the anti microbial integrity of the cleansing compositions; anti-acne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol), antibacterial agents and mixtures thereof. These materials can be used at ranges sufficient to provide the required benefit, as would be obvious to one skilled in the art.

The following examples describe certain embodiments of this invention, but the invention is not limited thereto. It should be understood that numerous changes to the disclosed embodiments could be made in accordance with the disclosure herein without departing from the spirit or scope of the invention. These examples are therefore not meant to limit the scope of the invention. Rather, the scope of the invention is to be determined only by the appended claims and their equivalents. In these examples all parts given are by weight unless otherwise indicated.

Example 1

Synthesis of DADMAC/DAA Copolymer

A 1-liter reactor equipped with a condenser, a thermometer, a nitrogen inlet and an overhead agitator is charged with 260 g of 66% DADMAC monomer, 34.5 g of diallylamine (DAA), 35.0 g of HCl solution, 6.0 g of deionized water, and 0.4 g of 20% Na$_4$EDTA solution. The polymerization mixture is purged with nitrogen and heated with agitation to a temperature of 80 C. An aqueous solution containing 2.1 g of ammonium persulfate (APS) is slowly fed to the reaction mixture over 190 minutes. The reaction temperature is allowed to increase to above 90 C and then maintained at 90 to 100 C during the APS feed period. After the APS feed, the reaction temperature is held at 95 C for about 30 minutes. Then an aqueous solution containing 6 g of sodium metabisulfite (MBS) is added over 30 minutes. The reaction mixture is held at 95 C for another 30 minutes to complete the polymerization (above 99% conversion). The polymer solution is then diluted with sufficient water to about 35% solids by weight and cooled to room temperature. The final product has a Brookfield viscosity of 9100 cps at 25 C (using a Brookfield LV4 spindle at 30 rpms) and 33% polymer solids.

Example 2

Synthesis of DADMAC/DM Copolymers

Following the same procedure as Example 1 the following polymers (in Table 1 below) are synthesized. The final product viscosities are measured at 25 C using a Brookfield viscometer using a Brookfield LVT #3 spindle at 12 rpms. The viscosity results are shown in Table 1 below.

TABLE 1

Co-PolyDADMAC/DAA with Varying DAA Content

| Sample | % DAA | % Solids | Viscosity (cps) | Weight Average Molecular Weight |
|---|---|---|---|---|
| 2A | 19.5 | 41.8 | 4900 | 88,000 |
| 2B | 9.75 | 40.9 | 8100 | 189,000 |
| 2C | 4.8 | 36.9 | 4000 | 376,000 |
| 2D | 7.5 | 37.7 | 11000 | 1,470,000 |
| 2E | 8.3 | 40.3 | Not Tested | Not Tested |
| 2F | 2.5 | 36.1 | Not Tested | Not Tested |

Example 3

DADMAC/DAA/Siloxane Terpolymer

A 0.5-liter reactor fitted with a mechanical stirrer, addition funnel and condenser is charged with 50 grams (14.5 mmol secondary amine, NH) of the base polymer (2D) from Example 2. 5.0 g of 2-propanol is added and heated to 70 C. The reactor content is adjusted with 1.3 g of 50% NaOH aqueous solution to a pH of 9.0 to 10.0 and heated to 70 C with agitation. After the pH adjustment, 0.5 g (5.8 mmol) of linear diepoxypolydimethylsiloxane (TEGO IS 4150, Degussa) is added into the reactor. The crosslinking reaction is maintained at about 70 C and the viscosity of the reaction solution is monitored with an agitator torque meter. The viscosity of the reactor contents, as is indicated by the torque meter reading, increases with reaction time. 3.5 g of 2-propanol was added to aid in viscosity reduction. While the viscosity shows little further increase with increasing reaction time after about four hours, the reaction mixture is held at 70 C for another 2 hours. The reaction mixture is heated to 90 C and the 2-propanol is distilled over. After distilling for 1 hour, the amount of 2-propanol remaining was less than 0.2% as determined by gas chromatography. A concentrated HCl solution and deionized water are added to adjust the pH to about 5. The resulting polymer product is a homogeneous, green-yellow emulsion-looking solution having 13.2 weight percent of polymer solids. The functionalized cationic terpolymer contains about 2.5 weight percent of the difunctional polysiloxane, which provides hydrophobic siloxane functionality to the copolymer.

Example 4

DADMAC/DAA/Siloxane Terpolymer

The procedure of Example 3 is followed except that 3.0 g instead of 0.5 g linear diepoxy polydimethylsiloxane (TEGO IS 4150, from Degussa) cross-linking agent is added. The resulting polymer product is a homogeneous, green-yellow emulsion-looking solution with 3.5 weight percent of polymer solids. The terpolymer contains about 13.3 weight percent of cross-linked polysiloxane which provides substantial hydrophobic siloxane functionality to the cationic terpolymer.

Example 5

DADMAC/DAA/Siloxane Terpolymer

The procedure of Example 3 is followed except that 1.5 g instead of 0.5 g cross-linking siloxane agent is added. The resulting polymer product is a homogeneous, green-yellow emulsion-looking solution with 11.3 weight percent of polymer solids. The terpolymer contains about 6.7 weight percent of crosslinked polysiloxane which provides substantial hydrophobic siloxane functionality to the cationic terpolymer.

Examples 6-13

DADMAC/DAA/Siloxane Terpolymers

The synthetic procedure of Example 3 is followed to produce the following cationic terpolymers, shown in Table 2.

TABLE 2

DADMAC/DAA/Siloxane Terpolymers

| Example | Polymer | Siloxane Component (Mol ratio[1]) | PerCent Polymer Solids Found |
|---|---|---|---|
| 6 | 2A | TEGO IS 4150 (0.11) | 5.5 |
| 7 | 2A | TEGO IS 4150 (0.2) | 6.0 |
| 8 | 2D | TEGO IS 4150 (0.2) | 3.4 |
| 9 | 2E | SILMER EP-Di-50[2] (0.05) | 12.7 |
| 10 | 2F | SILMER EP-Di-50 (0.04) | 14.2 |
| 11 | 2F | SILMER EP-Di-100[3] (0.03) | 8.6 |
| 12 | 2C | TEGO IS 4150[4] (0.3) | 13.4 |
| 13 | 2C | TEGO IS 4150 (0.5) | 15.1 |

[1]Based on diallylamine content.
[2]SILMER EP-Di-50 is a polydimethylsiloxane diepoxide copolymer with an average molecular weight of 4090 Daltons, available from Siltech Corp.
[3]SILMER EP-Di-100 is a polydimethylsiloxane diepoxide copolymer with an average molecular weight of 7800 Daltons, available from Siltech Corp.
[4]TEGO IS 4150 is a polydimethylsiloxane diepoxide copolymer which an average molecular weight of 850 Daltons, available from Degussa.

Example 14

DADMAC/DAA/Polyethylene Glycol Terpolymer

A 0.5-liter reactor fitted with a mechanical stirrer, addition funnel and condenser is charged with 26.9 grams (2.5 mmol secondary amine, NH) of the base polymer (2F) from Example 2. 33.9 g of water is added and heated to 70 C. The reactor content is adjusted with 0.1 g of 50% NaOH aqueous solution to a pH of 9.0 to 10.0 and heated to 70 C. with agitation. After the pH adjustment, 0.26 g (0.5 mmol) of linear polyethyleneglycol diglycidylether (PEGDGE, Aldrich Chemical, average molecular weight is 526 Daltons) is added into the reactor. The reaction is maintained at about 70 C and the viscosity of the reaction solution is monitored with an agitator torque meter. The viscosity of the reactor contents, as is indicated by the torque meter reading, increases with reaction time. Water (277.2 g) is added over the course of the reaction hold time to aid in viscosity reduction. While the viscosity shows little further increase with increasing reaction time after about four hours, the reaction mixture is held at 70 C for another 2 hours. After a total reaction time of six hours at 70 C, the level of PEGDGE remaining is determined to by 0% by gas chromatography. A concentrated HCl solution and deionized water are added to adjust the pH to about 4. The resulting polymer product is a homogeneous, yellow emulsion-looking solution having 3.4 weight percent of polymer solids.

Examples 15-17

DADMAC/DAA/Polyalkylene Glycol Terpolymers

The synthetic procedure of Example 14 is followed to produce the following cationic terpolymers, shown in Table 3.

TABLE 3

Cationic DADMAC/DAA/Glycol Terpolymers

| Example | Polymer | Glycol Component (Mol ratio[1]) | PerCent Polymer Solids Found |
|---|---|---|---|
| 15 | 2F | PPGDGE (0.5) | 3.1 |
| 16 | 2F | PEGDGE (0.8) | 8.7 |
| 17 | 2F | PEGDGE (0.11) | 7.7 |

[1]Based on diallylamine content.
[2]PPGDGE is polypropyleneglycoldiglycidyl ether with an average molecular weight of 380 Daltons, available from Aldrich Chemical Company.
[3]PEGDGE is polyethyleneglycoldiglycidyl ether with an average molecular weight of 526 Daltons, available from Aldrich Chemical Company.

Example 18

DADMAC/DAA/Siloxane Terpolymers Further Functionalized with C12-Alkyl Substituted Quaternary Ammonium Group 50.0 g (42 mmol/eq. wt. based on DM in sample) of the base polymer 2A from Example 2, 10.1 g of deionized water and 3.3 g 50% NaOH solution are placed into a round-bottomed flask equipped with a stirrer, nitrogen inlet and a thermoregulator and heated. When the temperature reaches 70 C, 30.2 g (33.5 mmol) of a 38% solution of 3-chloro-2-hydroxypropyl-dimethyldodecylammonium chloride (QUAB 342 from Degussa) and 8 g of 2-propanol are added to the flask. An exotherm is observed with an increase in temperature from 65-70 C. When the rise in temperature subsides, the reaction mixture is maintained at 65 C for three hours with stirring. During the reaction 6.0 g of deionized water is added to aid in viscosity control. At this time the consumption of QUAB 342 is determined to be >99% by chloride titration. After this time, the mixture is cooled to room temperature and 179 g of deionized water and 1.5 g of a 2.3% HCl/water solution is added to adjust the pH. The functionalized DADMAC/DAA copolymer is obtained as a clear viscous yellow mixture of 12.8 wt. % solids. The intermediate product has a Brookfield viscosity of 4900 cps at 25 C (using a Brookfield LV3 spindle at 12 rpms) at 12.8% polymer solids.

An aliquot of the reaction mass (20.1 g) is taken and added to a separate reaction flask and the procedure of Example 3 is followed except that 0.2 g instead of 0.5 g linear diepoxy polydimethylsiloxane (TEGO IS 4150, from Degussa) reactant is added. The resulting terpolymer product is a homogeneous, yellow emulsion-looking solution with 3.4 weight percent of polymer solids.

Examples 19

DADMAC/DAA/Siloxane Terpolymers Further Functionalized

The synthetic procedure of Example 18 is followed generally to produce the following cationic terpolymers, shown in Table 4.

TABLE 4

Functionalized DADMAC/DAA/Siloxane Terpolymers

| Example | Polymer | Siloxane component (Mol ratio[1]) | Grafted component (Mol ratio[1]) |
|---|---|---|---|
| 19 | 2A | TEGO IS 4150 (0.08) | QUAB 342 (0.8) |
| 20 | 2B | TEGO IS 4150 (0.11) | QUAB 342 (0.3) |
| 21 | 2A | TEGO IS 4150 (0.2) | QUAB 342 (0.5) |
| 22 | 2B | TEGO IS 4150 (0.2) | QUAB 342 (0.1) |
| 23 | 2A | SILMER EP-Di-50[2] (0.05) | QUAB 151 (0.5) |
| 24 | 2C | SILMER EP-Di-50 (0.04) | QUAB 151 (0.2) |
| 25 | 2D | SILMER EP-Di-100[3] (0.03) | QUAB 151 (0.4) |
| 26 | 2B | TEGO IS 4150[4] (0.3) | QUAB 426 (0.3) |
| 27 | 2A | TEGO IS 4150 (0.5) | QUAB 426 (0.5) |
| 28 | 2A | TEGO IS 4150 (0.11) | AO (0.3) |
| 29 | 2A | TEGO IS 4150 (0.2) | QUAB 426 (0.1) |
| 30 | 2D | TEGO IS 4150 (0.2) | BZT (0.4) |
| 31 | 2D | SILMER EP-Di-50[2] (0.05) | E-dodecane (0.1) |
| 32 | 2B | SILMER EP-Di-50 (0.04) | Glycidol TEMPO (0.4) |
| 33 | 2F | SILMER EP-Di-100[3] (0.03) | E-hexane (0.2) |
| 34 | 2B | TEGO IS 4150[4] (0.3) | PGE (0.4) |
| 35 | 2C | TEGO IS 4150 (0.5) | PSA (0.5) |
| 36 | 2E | SILMER EP-Di-50[2] (0.05) | CA (0.6) |
| 37 | 2A | SILMER EP-Di-50 (0.04) | PEG 350 (0.4) |
| 38 | 2A | SILMER EP-Di-100[3] (0.03) | Dodecenyl SA (0.5) |
| 39 | 2C | TEGO IS 4150 | Succinic Anhydride (0.5) |
| 40 | 2A | TEGO IS 4150 | Phthalic Anhydride (0.4) |

[1]Based on diallylamine content
[2]SILMER EP-Di-50 is a polydimethylsiloxane diepoxide copolymer with an average molecular weight of 4090 Daltons, available from Siltech Corp.
[3]SILMER EP-Di-100 is a polydimethylsiloxane diepoxide copolymer with an average molecular weight of 7800 Daltons, available from Siltech Corp.
[4]TEGO IS 4150 is a polydimethylsiloxane diepoxide copolymer which an average molecular weight of 850 Daltons, available from Degussa.
Glycidol TEMPO = 1-oxy-2,2,6,6,-tetramethyl-4-glycidyloxypiperidine
QUAB 342 = 3-chloro-2-hydroxypropyl-dimethyldodecylammonium chloride, Degussa
QUAB 151 = glycidyltrimethylammonium chloride, Degussa
QUAB 426 = 3-chloro-2-hydroxypropyl-dimethyloctadecylammonium chloride, Degussa
E-Dodecane = 1,2-epoxydodecane
E-Hexane = 1,2-epoxyhexane
PGE = Phenyl glycidyl ether
PSA = 3-chloro-2-hydroxy-1-propane sulfonic acid, Na salt.
CA = 2-Chloroacetamide
PEG 350 = CARBOWAX 350 = polyethylene glycol 350
Dodecenyl SA = 2-Dodecen-1-yl succinic anhydride
BZT = Benzotriazole UV absorber which is covalently attached to the terpolymer
AO = phenolic antioxidant which is covalently attached to the terpolymer

Examples 41-44

Hair Conditioning Formulations

Hair conditioning formulations are prepared according to Table 5.

TABLE 5

Hair Conditioning Formulations

| Ingredients, wt % | Typical Range Based on Activity | 41 | 42 | 43 | 44 |
|---|---|---|---|---|---|
| Water | qs to 100% | qs to 100% | qs to 100% | qs to 100% | qs to 100% |
| *Conditioning Agent* | | | | | |
| Guar Hydroxypropyltrimonium Chloride | 0-2% | | | | |
| Polyquaternium-10 | 0-5% | | | | |
| Acrylamidopropyltrimonium Chloride/Acrylamide Copolymer | 0-0.5% | 0.05 | | | 0.5 |
| Cationic Terpolymer of Examples 1-40 | 0-10% | 3.0 | 1.0 | 2.0 | 5.0 |
| *Thickeners* | | | | | |
| Polyquaternium 37 and Mineral Oil and PPG-1 Trideceth-6 | 0-5% | 3.0 | 2.0 | | 2.5 |
| Polyquaternium 37 and Propylene Dicaprylate Dicaprate and PPG-1 Trideceth-6 | 0-5% | | | 1.0 | |
| *Waxes, alcohols & emulsifiers* | | | | | |
| PEG-45 Palm Kernel Glycerides | 0-5% | 0.5 | — | 1.0 | — |
| Glycereth-31 | 0-10% | 1.0 | 2.0 | — | 1.0 |
| PPG-5-Ceteth-20 | 0-5% | — | 0.5 | — | 0.5 |
| Glyceryl Stearate and PEG-100 Stearate | 0-10% | 1.0 | — | 1.5 | — |
| Cetyl Alcohol | 0-10% | 1.0 | — | 0.5 | 1.0 |
| Glycol Stearate | 0-10% | 2.0 | 1.0 | — | 2.0 |
| Ethylene Glycol Distearate | 0-10% | — | 2.0 | 1.0 | — |
| *Esters/Silicones* | | | | | |
| Dimethicone PEG-8 Meadowfoamate | 0-5% | — | 1.0 | 2.0 | 3.0 |
| Amodimethicone | 0-5% | | 2.0 | | |
| *Vitamins* | | | | | |
| Tocopherol | 0-1% | 0.1 | 0.1 | — | — |
| Panthenol | 0-1% | — | 0.1 | 0.1 | 0.1 |
| Fragrance | 0-2% | 0.5 | 0.5 | 0.5 | 0.5 |
| *Chelating Agent* | | | | | |
| Disodium EDTA | <0.10% | 0.1 | 0.1 | — | — |
| Tetrasodium EDTA | <0.10% | — | — | 0.1 | 0.1 |
| *pH Adjuster* | | | | | |
| NaOH | <0.50% | qs to 4.5-5.5 | qs to 4.5-5.5 | qs to 4.5-5.5 | qs to 4.5-5.5 |
| TEA | <0.50% | qs to 4.5-5.5 | qs to 4.5-5.5 | qs to 4.5-5.5 | qs to 4.5-5.5 |
| *Preservative* | | | | | |
| DMDM Hydantoin | 0-1% | 1.0 | 1.0 | — | — |
| Phenoxyethanol and Methylparaben and Propylparaben and Butylparaben and Isobutylparaben | 0-1% | — | — | 1.0 | 1.0 |

Examples 45-48

Lotion/Cream Formulation

Lotions and/or cream formulations are prepared according to Table 6.

TABLE 6

Lotions and/or Cream Formulations

| Ingredients, wt % | Typical Range Based on Activity | 45 | 46 | 47 | 48 |
|---|---|---|---|---|---|
| Water | qs to 100% | qs to 100% | qs to 100% | qs to 100% | qs to 100% |
| Humectant | | | | | |
| Glycerin | 0-10% | 5.0 | 2.5 | — | 4.0 |
| Propylene Glycol | 0-5% | — | 1.0 | 1.5 | 2.0 |
| Conditioner | | | | | |
| Cationic Terpolymers of Examples 1-40 | 0-5% | 2.5 | 1.0 | 5.0 | 4.0 |
| Thickening agent | | | | | |
| Carbomer | 0-1% | — | — | — | 0.8 |
| Polyacrylamide and C13-14 Isoparaffin and Laureth-7 | 0-5% | — | — | 0.8 | — |
| Acrylates/Beheneth-25 Methacrylate Copolymer | 0-5% | — | 2.5 | — | — |
| Sodium Acrylates Copolymer and Mineral Oil and PPG-1 Trideceth-6 | 0-3% | 1.0 | — | — | — |
| Emulsifiers | | | | | |
| Glyceryl Stearate | 0-5% | 3.0 | 1.0 | 1.0 | 1.5 |
| Steareth-2 | 0-5% | — | — | 0.7 | — |
| PEG-100 Stearate | 0-5% | 2.0 | — | 0.5 | — |
| Waxes | | | | | |
| Cetyl Alcohol | 0-5% | 2.0 | 1.0 | — | 1.0 |
| Cetearyl Alcohol | 0-5% | — | — | — | 1.5 |
| Stearyl Alcohol | 0-5% | — | — | 1.0 | — |
| Fatty Acids | | | | | |
| Stearic Acid | 0-10% | — | 2.5 | — | 3.0 |
| Behenic Acid | 0-10% | — | — | 1.0 | — |
| Oils/Esters | | | | | |
| Caprylic/Capric Triglyceride | 0-10% | 2.0 | 1.5 | — | 2.0 |
| Decyl Oleate | 0-5% | — | 0.5 | 0.8 | 1.5 |
| Cetyl Palmitate | 0-5% | 1.0 | 0.5 | — | 1.0 |
| Silicone | | | | | |
| Cyclomethicone | 0-5% | 1.0 | 1.0 | 4.0 | 2.0 |
| Dimethicone | 0-5% | — | — | — | 0.8 |
| Vitamins | | | | | |
| Tocopherol | 0-1% | 0.1 | — | 0.1 | 0.1 |
| Panthenol | 0-1% | — | 0.1 | — | 0.1 |
| Fragrance | 0-2% | 0.5 | 0.5 | 0.5 | 0.5 |
| Chelating Agent | | | | | |
| Disodium EDTA | <0.10% | 0.1 | — | 0.1 | — |
| Tetrasodium EDTA | <0.10% | — | 0.1 | — | 0.1 |
| pH Adjuster | | | | | |
| TEA | <0.50% | qs to 5.5-6.5 | qs to 5.5-6.5 | qs to 5.5-6.5 | qs to 5.5-6.5 |
| Preservative | | | | | |
| DMDM Hydantoin | 0-1% | — | — | 1.0 | — |
| Phenoxyethanol and Methylparaben and Propylparaben and Butylparaben and Isobutylparaben | 0-1% | 1.0 | 1.0 | — | 1.0 |

Example 49

2 in 1 Shampoo Formulation

Table 7 gives a formulation for a 2 and 1 shampoo. The inventive cationic terpolymers are added to the formulation below at 0.05 and 0.1 weight percent concentration. The formulations below incorporating the cationic terpolymer are compared to control shampoo formulations wherein the inventive cationic terpolymer is replaced with a cationic polymer at 0.05 and 0.1 weight % (cationic cellulose, Polyquaternium 10 or Guar hydroxypropyl trimethylammonium chloride) and 2 weight % polydimethylsiloxane.

TABLE 7

2 in 1 Shampoo Formulations

| Component | Weight % |
|---|---|
| Water | qs to 100% |
| ALES-3[1] | 10 |
| ALS[2] | 4 |
| Cocamidopropyl Betaine | 3 |
| Ethylene Glycol distearate | 2 |
| Cetyl Alcohol | 1.5 |
| Cocamide MEA | 1.0 |
| Cationic Terpolymer of the Present Invention (Examples 1-40) | 0.10 and 0.05 |

[1]Ammonium lauryl ether (3 ethoxylate untis) sulfate.
[2]Ammonium lauryl sulfate.

The shampoo pH is adjusted to 5.5. Sodium chloride is used to adjust the viscosity of the shampoos to approximately 6000 cps. The control formulations with polysiloxane and Polyquaternium 10 or Guar hydroxypropyl trimethylammonium chloride polyquaternium 10 are homogenized until a polysiloxane droplet size ranging from 0.1 to about 20.0 microns are attained.

The measured values of hair treated with the inventive terpolymers and the results for substantivity and build-up of silicone, and reductions in wet and dry combing energies on hair demonstrate the excellent conditioning properties of the inventive cationic terpolymers in a 2 in 1 shampoo formulation.

Examples 51-52

2 in 1 Shampoo Formulations

Examples 51 and 51 are formulated in the 2 and 1 shampoo as in Table 7 except the inventive cationic terpolymers are added at 0.5 wt. %. Comparisons are made using the cationic terpolymer alone and in combination with a cationic potato starch.

Example 53

Facial Moisturizer Formulation

A facial moisturizer formulation is prepared comprising the list of ingredients below.

| Facial Moisturizer Formulation | |
|---|---|
| Ingredient | Amount (wt-%) |
| Aqua | qs to 100 |
| Cationic Terpolymer of the Present Invention (Examples 1-40) | 2.00 |
| Coco-caprylate/Caprate | 2.50 |
| Squalane | 2.00 |
| Hexyl Laurate | 2.00 |
| Ethylhexyl Palmitate | 2.00 |
| Dimethicone | 2.50 |
| Ethylhexyl Methoxycinnamate | 5.00 |
| Parfum | 0.20 |
| Preservative | 0.20 |

Example 54

Body Moisturizer Formulation

A body moisturizer formulation is prepared comprising the list of ingredients below.

| Body Moisturizer Formulation | |
|---|---|
| Ingredient | Amount (wt-%) |
| Aqua | qs to 100 |
| Cationic Terpolymer of the Present Invention (Examples 1-40) | 1.00 |
| Stearyl Alcohol | 5.00 |
| Cetyl Alcohol | 5.00 |
| Dimethicone | 5.00 |
| Cetearyl Stearate | 2.00 |
| Glycerin | 2.00 |
| Propylene Glycol | 2.00 |
| Parfum | 0.20 |
| Preservative | 0.20 |

Example 55

Spray Moisturizer Formulation

A spray moisturizer formulation is prepared comprising the list of ingredients below.

| Spray Moisturizer Formulation | |
|---|---|
| Ingredient | Amount (wt-%) |
| Aqua | qs to 100 |
| Cationic Terpolymer of the Present Invention (Examples 1-40) | 1.50 |
| Cyclomethicone | 3.00 |
| Hydrogenated Polydecene | 5.00 |
| Isostearyl Lactate | 1.50 |
| Sodium Hyaluronate | 1.00 |
| Glyceryl Myristate | 1.00 |
| Parfum | 0.20 |
| Preservative | 0.20 |

Example 56

Leave-On Conditioner Formulation

A leave-on conditioner formulation is prepared comprising the list of ingredients below.

| Leave-on Conditioner Formulation | |
|---|---|
| Ingredient | Amount (wt-%) |
| Aqua | qs to 100 |
| Cationic Terpolymer of the Present Invention (Examples 1-40) | 1.50 |
| Propylene Glycol | 2.00 |
| Glycerin | 2.00 |
| Dimethicone Copolyol | 2.00 |
| Preservative | 0.25 |
| Parfum | 0.30 |
| Ethylhexyl Methoxycinnamate | 2.00 |

Example 57

Silicone Conditioner Formulation

A silicone conditioner formulation is prepared comprising the list of ingredients below.

| Silicone Conditioner Formulation | |
|---|---|
| Ingredient | Amount (wt-%) |
| Aqua | qs to 100 |
| Cationic Terpolymer of the Present Invention (Examples 1-40) | 2.00 |
| Cyclopentasiloxane (and) Dimethiconol | 2.00 |
| Cyclomethicone | 2.00 |
| Ceteareth-5 | 0.75 |
| Preservative | 0.20 |
| Dimethicone PEG-8 Meadowfoamate | 0.50 |
| Parfum | 0.20 |

Example 58

Rinse-Off Conditioner Formulation

A rinse-off conditioner formulation is prepared comprising the list of ingredients below.

| Rinse-Off Conditioner Formulation | |
|---|---|
| Ingredient | Amount (wt-%) |
| Aqua | qs to 100 |
| Cationic Terpolymer of the Present Invention (Examples 1-40) | 2.00 |
| Decyl Oleate | 2.00 |
| *Helianthus Annuus* | 2.50 |
| Dimethicone (and) Dimethiconol | 2.50 |
| Preservative | 0.20 |
| Parfum | 0.30 |
| CI 18965 | 0.02 |
| Sodium Benzotriazolyl Butylphenol Sulfonate (and) Buteth-3 (and) Tributyl Citrate | 0.20 |

Example 59

Sunless Tanning Cream with Sunscreen Formulation

A sunless tanning cream with sunscreen formulation is prepared comprising the list of ingredients below.

| Sunless Tanning Cream with Sunscreen Formulation | |
|---|---|
| Ingredient | Amount (wt-%) |
| Aqua | qs to 100 |
| Cationic Terpolymer of the Present Invention (Examples 1-40) | 2.00 |
| Ethylhexyl Methoxycinnamate | 5.00 |
| Dihydroxyacetone | 3.00 |
| Methylene bis-Benzotriazolyl Tetramethyl Butylphenol | 3.00 |
| Paraffinum Liquidum | 7.50 |
| Preservative | 0.50 |
| Glycerin | 2.00 |
| Parfum | 0.50 |

Example 60

Moisturizing Lipstick Formulation

A moisturizing lipstick formulation is prepared comprising the list of ingredients below.

| Moisturizing Lipstick Formulation | |
|---|---|
| Ingredient | Amount (wt-%) |
| *Ricinus Communis* | 25.00 |
| *Euphorbia Cerifera* | 5.40 |
| *Copernicia Cerifera* | 4.00 |
| Ozokerite | 5.00 |
| Hydrogenated Lanolin | 11.10 |
| Microcrystalline Wax | 4.50 |
| Cationic Terpolymer of the Present Invention (Examples 1-40) | 2.25 |
| Octyldodecanol | 6.60 |
| Isocetyl Palmitate | 5.00 |
| Beeswax | 2.00 |
| Cetearyl Alcohol | 20.00 |
| Preservative | 0.10 |
| Tetradibutyl Pentaerythrityl Hydroxyhydrocinnamate | 0.05 |
| Pigment | 9.00 |

Example 61

Moisturizing Soap Base Formulation

A moisturizing soap base formulation is prepared comprising the list of ingredients below.

| Moisturizing Soap Base Formulation | |
|---|---|
| Ingredient | Amount (wt-%) |
| Cationic Terpolymer of the Present Invention (Examples 1-40) | 1.00 |
| Sodium Tallowate (and) Sodium Cocoate | 98.10 |
| Tetrasodium EDTA | 0.10 |

| Moisturizing Soap Base Formulation | |
|---|---|
| Ingredient | Amount (wt-%) |
| Titanium Dioxide | 0.10 |
| Tetradibutyl Pentaerythrityl Hydroxyhydrocinnamate | 0.05 |
| Parfum | 0.50 |

Example 62

Anti-Acne Skin Cream Formulation

An anti-acne skin cream formulation is prepared comprising the list of ingredients below.

| Anti-Acne Skin Cream Formulation | |
|---|---|
| Ingredient | Amount (wt-%) |
| Aqua | qs to 100 |
| Cationic Terpolymer of the Present Invention (Examples 1-40) | 4.00 |
| Alcohol | 5.00 |
| Isocetyl Palmitate | 2.00 |
| Salicylic Acid | 2.00 |
| Paraffinum Liquidum | 1.00 |
| Preservative | 0.50 |
| Glycerin | 2.00 |
| Parfum | 0.50 |

Example 63

Conditioner Formulation

A conditioner formulation is prepared comprising the list of ingredients below.

| Conditioner Formulation | |
|---|---|
| Ingredient | Amount (wt-%) |
| Aqua | qs to 100 |
| Glycerin | 5.00 |
| DMDM Hydantoin | 0.50 |
| Methylparaben | 0.20 |
| Polysorbate 80 | 1.00 |
| Parfum | 0.20 |
| Phenoxyethanol | 0.50 |
| Polyquaternium-6 | 2.00 |
| Cationic Terpolymer of the Present Invention (Examples 1-40) | 5.60 |

What is claimed is:

1. A personal care composition comprising
(a) an effective amount of at least one crosslinked cationic terpolymer of formula (I)

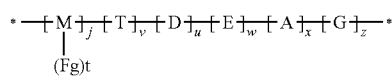

(I)

wherein
j, t, u, v, w, x, and z represent the percentage by weight that each repeating unit or derived monomer is contained within the cationic terpolymer;
* is a terminal group, for example a catalyst residue;
j, t, u, v, w, x, and z add up to total 100 percent and are based on weight of the terpolymer;
j, u and x are independently from 0.0001 to 39.9997% based on weight of the terpolymer;
j+u+x is at least 2.5 to 39.9999% percent based on the weight of the terpolymer;
w is from about 0.0001% to about 20% by weight of the terpolymer;
t is from about 0% to about 20% by weight of the terpolymer;
z and v are independently from about 0.0001 to about 60% based on weight of the terpolymer;
z+v is equal to or greater than 60 percent based on the weight of the terpolymer;
E is derived from a difunctional siloxane monomer of formula (II)

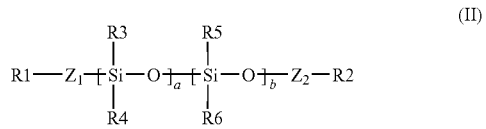

(II)

wherein R1 and R2 independently are a polymerizable function from the group of the vinylically unsaturated compounds which is suitable for the synthesis of polymeric structures by a free-radical route or by condensation and represents vinyl, allyl, methallyl, methylvinyl, acryloyl (CH2=CH—CO—), methacryloyl (CH2=C[CH3]—CO—), crotonyl, senecionyl, itaconyl, maleyl, fumaryl, epoxy or styryl radicals;
Z1 is a direct bond or a bridging group selected from the group consisting of —O—, —((C1-C50)alkylene), —((C6-C30)arylene)-, —((C5-C8)cycloalkylene)-, —((C1-C50)alkenylene)-, -(polypropylene oxide)n-, -(polyethylene oxide)o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;
Z2 is a direct bond or a bridging group selected from the group consisting of —((C1-C50)alkylene), —((C6-C30)arylene)-, —((C5-C8)cycloalkylene)-, —((C1-C50)alkenylene)-, -(polypropylene oxide)n-, -(polyethylene oxide)o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;
R3, R4, R5, and R6 are independently straight or branched alkyl chain of 1 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl groups of 1 to 4 carbon atoms; or said alkyl substituted by one or more —OH, —OCO—$R_{10}$, —O$R_{10}$, or —NH$_2$ groups or mixtures thereof; or said alkyl interrupted by one or more —O—, —NH— or —N$R_{10}$— groups or mixtures thereof and which can be unsubstituted or substituted by one or more —OH, —OR$_{10}$ or —NH$_2$ groups or mixtures thereof; or OR$_{11}$;

R$_{10}$ is straight or branched chain alkyl of 1 to 24 carbon atoms or phenyl or benzyl;

R$_{11}$ is straight or branched chain alkyl of 1 to 24 carbon atoms or phenyl or benzyl; or said alkyl substituted by one or more —OH, —OCO—R$_{10}$, —OR$_{10}$, or —NH$_2$ groups or mixtures thereof; or said alkyl interrupted by one or more —O—, —NH— or —NR$_{10}$— groups or mixtures thereof and which can be unsubstituted or substituted by one or more —OH, —OR$_{10}$ or —NH$_2$ groups or mixtures thereof;

a and b represent stoichiometric coefficients which amount independently of one another to from 1 to 5000;

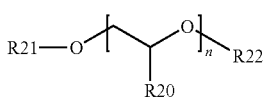

wherein the difunctional silicone monomer of formula (II) crosslinks the amines of monomer M, D or A of formula (III), and the difunctinal silicone is used in an amount ranging from 0.03 to 1.0 moles of the amines of monomer M, D or A of formula (III);

Fg is the residue from at least one functional reactant grafted onto the amino-functional groups of the cationic amino base polymer, wherein the functional reactant is selected from the group consisting of epoxy compounds, haloalkyl compounds, isocyanate compounds and compound containing activated olefinic double bonds;

G and T are independently derived from a monomer selected from the group consisting of diallyldimethyl ammonium chloride (DADMAC), diallyldimethyl ammonium bromide, diallyldimethyl ammonium sulfate, diallyldimethyl ammonium phosphates, dimethallyldimethyl ammonium chloride, diethylallyl dimethyl ammonium chloride, diallyl di(beta-hydroxyethyl) ammonium chloride, and diallyl di(beta-ethoxyethyl) ammonium chloride;

M, D and A are independently derived from a monomer of formula (III)

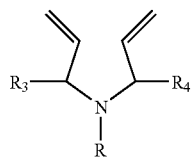

where R, R$_3$ and R$_4$ are, independently of each other, hydrogen or C$_1$-C$_4$alkyl; and (b) a cosmetically acceptable adjuvant.

2. A composition according to claim 1 wherein

M, D and A of formula (I) are independently derived from a monomer selected from the group consisting of diallylamine, 2,2'-dimethyl diallylamine, 2,2'-diethyl diallylamine, 2,2'-diisopropyl diallylamine, 2,2'-dipropyl diallylamine, 2,2'-diisobutyl diallylamine, N-methyl diallylamine, N-ethyl diallylamine, 2,2'-dimethyl-N-methyl diallylamine, 2,2'-diethyl-N-methyl diallylamine, 2,2'-diisoprpyl-N-methyl diallylamine, 2,2'-dipropyl-N-methyl diallylamine, 2,2'-dimethyl-N-ethyl diallylamine, and 2,2'-diethyl-N-ethyl diallylamine;

G and T of formula (I) are independently derived from a monomer selected from the group consisting diallyldimethyl ammonium chloride, diallyldimethyl ammonium sulfate, dimethallyldimethyl ammonium chloride, diethylallyl dimethyl ammonium chloride, diallyl di(beta-hydroxyethyl) ammonium chloride, and diallyl di(beta-ethoxyethyl) ammonium chloride;

E of formula (I) is derived from a difunctional siloxane monomer of formula (II)

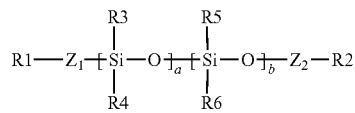

R1 and R2 independently are vinyl, allyl, methallyl, methylvinyl, acryloyl (CH2=CH—CO—), methacryloyl (CH2=C[CH3]—CO—), or epoxy;

Z1 is a direct bond or a bridging group selected from the group consisting of —((C1-C18)alkylene), —((C6-C10)arylene)-, —((C5-C8)cycloalkylene)-, -(polypropylene oxide)n-, -(polyethylene oxide)o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;

Z2 is a direct bond or a bridging group selected from the group consisting of —((C1-C18)alkylene), —((C6-C10)arylene)-, —((C5-C8)cycloalkylene)-, -(polypropylene oxide)n-, -(polyethylene oxide)o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;

R3, R4, R5, and R6 are independently straight or branched alkyl chain of 1 to 12 carbon atoms, cycloalkyl of 5 to 12 carbon atoms, phenyl; or said alkyl substituted by one or more —OH, —OCO—R$_{10}$, —OR$_{10}$, or —NH$_2$ groups or mixtures thereof; or said alkyl interrupted by one or more —O—, —NH— or —NR$_{10}$— groups or mixtures thereof and which can be unsubstituted or substituted by one or more —OH, —OR$_{10}$ or —NH$_2$ groups or mixtures thereof; or OR$_{11}$;

R$_{10}$ is straight or branched chain alkyl of 1 to 24 carbon atoms or phenyl or benzyl;

R$_{11}$ is straight or branched chain alkyl of 1 to 12 carbon atoms;

a and b represent stoichiometric coefficients which amount independently of one another to from 1 to 5000;

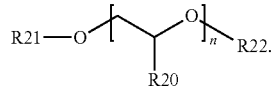

3. A composition according to claim 2 wherein
M, D and A of formula (I) are independently derived from a monomer selected from the group consisting of diallylamine and N-methyl diallylamine;
G and T of formula (I) are diallyldimethyl ammonium chloride;
E of formula (I) is derived from a difunctional siloxane monomer of formula (II)

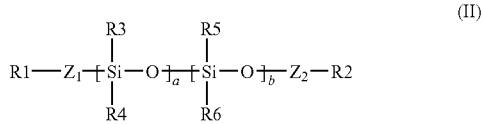

R1 and R2 independently are vinyl, allyl, methallyl, methylvinyl, acryloyl (CH2=CH—CO—), methacryloyl (CH2=C[CH3]—CO—), or epoxy;
Z1 is a direct bond or a bridging group selected from the group consisting of —O—, —((C1-C12)alkylene, —((C5-C8)cycloalkylene)-, —((C1-C10)alkyl)-(Si(OCH3)2)- and —(Si(OCH3)2)-;
Z2 is a direct bond or a bridging group selected from the group consisting of —O—, —((C1-C12)alkylene, —((C5-C8)cycloalkylene)-, —((C1-C10)alkyl)-(Si(OCH3)2)- and —(Si(OCH3)2)-;
R3, R4, R5, and R6 are independently straight or branched alkyl chain of 1 to 12 carbon atoms, phenyl; or $OR_{11}$;
R11 is straight or branched chain alkyl of 1 to 12 carbon atoms;
a and b represent stoichiometric coefficients which amount independently of one another to from 1 to 5000;

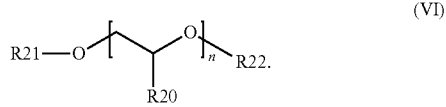

4. A composition according to claim 1 wherein the weight average molecular weight of the cationic terpolymer of component (a) formula (I) is from about 1,000 to about 10 million Daltons.

5. A composition according to claim 4 wherein the weight average molecular weight of the cationic polymer of component (a) formula (I) is from about 25,000 to about 5 million Daltons.

6. A composition according to claim 5 wherein the weight average molecular weight of the cationic polymer of component (a) formula (I) is from about 40,000 to about 4 million Daltons.

7. A composition according to claim 6 wherein the weight average molecular weight of the cationic polymer of component (a) formula (I) is from about 50,000 to about 2 million Daltons.

8. A composition according to claim 1 wherein the cationic terpolymers of formula (I) component (a) are in the form of particles and have a particle size from about 0.001 to about 500 micrometers.

9. A composition according to claim 8 wherein the cationic terpolymers of formula (I) component (a) are in the form of particles and have a particle size from about 0.01 to about 300 micrometers.

10. A composition according to claim 9 wherein the cationic terpolymers of formula (I) component (a) are in the form of particles and have a particle size from about 1 to about 300 micrometers.

11. A composition according to claim 1 further comprising
(c) at least one compound selected from the group consisting of the ultraviolet light absorbers, antioxidants, tocopherol, tocopherol acetate, hindered amine light stabilizers, complex formers, optical brighteners, surfactants, and polyorganosiloxanes.

12. A composition according to claim 11 where the ultraviolet light absorbers are selected from the group consisting of 2H-benzotriazoles, s-triazines, benzophenones, alpha-cyanoacrylates, oxanilides, benzoxazinones, benzoates and alpha-alkyl cinnamates.

13. A composition according to claim 1 further comprising
(d) a dye or a pigment or mixtures thereof.

14. A composition according to claim 1 wherein the cationic terpolymer of formula (I) component (a) is present in a concentration of about 0.0001 weight % to about 50 weight % based on the total composition.

15. A composition according to claim 14 where the cationic terpolymer of formula (I) component (a) is present in a concentration of about 0.01 weight % to about 25 weight % based on the total composition.

16. A composition according to claim 15 where the cationic terpolymer of formula (I) component (a) is present in a concentration of about 0.1 weight % to about 7 weight % based on the total composition.

17. A composition according to claim 16 where the cationic terpolymer of formula (I) component (a) is present in a concentration of about 0.2 weight % to about 5 weight % based on the total composition.

18. A composition according to claim 1 wherein the personal care composition is a product selected from the group consisting of skin-care products, bath and shower products, liquid soaps, bar soaps, preparations containing fragrances and odoriferous substances, hair-care products, dentifrices, deodorizing and antiperspirant preparations, decorative preparations, light protection formulations and preparations containing active ingredients, shaving lotions, body oils, body lotions, body gels, treatment creams, skin protection ointments, shaving preparations, skin powders, shampoos, hair conditioners, 2 in 1 conditioners, leave in and rinse off conditioners, agents for styling and treating hair, hair perming agents, relaxants, hair sprays and lacquers, permanent hair dyeing systems, semi-permanent hair dyeing systems, temporary hair dyeing systems, hair bleaching agents, lipsticks, nail varnishes, eye shadows, mascaras, dry and moist make-up, rouge, powders, depilatory agents, sun care and after sun products.

19. A method for the conditioning treatment of mammalian keratin-containing fibers, wherein said method comprises contacting said fibers with an effective amount of a personal care composition comprising one or more cationic terpolymers of formula (I) according to claim 1.

20. A method for the conditioning treatment of mammalian skin, wherein said method comprises contacting said skin with an effective amount of a personal care composition comprising one or more cationic terpolymers of formula (I) according to claim 1.

21. A crosslinked cationic terpolymer of formula (I)

$$*-[M]_j-[T]_v-[D]_u-[E]_w-[A]_x-[G]_z-*$$
$$\phantom{xxxxx}|$$
$$\phantom{xxxxx}(Fg)_t$$
(I)

wherein j, t, u, v, w, x, and z represent the percentage by weight that each repeating unit or derived monomer is contained within the cationic terpolymer;

* is a terminal group, for example a catalyst residue;

j, t, u, v, w, x, and z add up to total 100 percent and are based on weight of the terpolymer;

j, u and x are independently from 0.0001 to 39.9997% based on weight of the terpolymer;

j+u+x is at least 2.5 to 39.9999% percent based on the weight of the terpolymer;

w is from about 0.0001% to about 20% by weight of the terpolymer;

t is from about 0% to about 20% by weight of the terpolymer;

z and v are independently from about 0.0001 to about 60% based on weight of the terpolymer;

z+v is equal to or greater than 60 percent based on the weight of the terpolymer;

E is derived from a difunctional siloxane monomer of formula (II)

$$R1-Z_1-[Si(R3)(R4)-O]_a-[Si(R5)(R6)-O]_b-Z_2-R2$$
(II)

R1 and R2 independently are a polymerizable function from the group of the vinylically unsaturated compounds which is suitable for the synthesis of polymeric structures by a free-radical route or by condensation and represents vinyl, allyl, methallyl, methylvinyl, acryloyl (CH2=CH—CO—), methacryloyl (CH2=C[CH3]—CO—), crotonyl, senecionyl, itaconyl, maleyl, fumaryl, epoxy or styryl radicals;

Z1 is a direct bond or a bridging group selected from the group consisting of —O—, —((C1-C50)alkylene), —((C6-C30)arylene)-, —((C5-C8)cycloalkylene)-, —((C1-C50)alkenylene)-, -(polypropylene oxide)n-, -(polyethylene oxide)o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;

Z2 is a direct bond or a bridging group selected from the group consisting of —((C1-C50)alkylene), —((C6-C30)arylene)-, —((C5-C8)cycloalkylene)-, —((C1-C50)alkenylene)-, -(polypropylene oxide)n-, -(polyethylene oxide)o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;

R3, R4, R5, and R6 are independently straight or branched alkyl chain of 1 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl groups of 1 to 4 carbon atoms; or said alkyl substituted by one or more —OH, —OCO—$R_{10}$, —$OR_{10}$, or —$NH_2$ groups or mixtures thereof; or said alkyl interrupted by one or more —O—, —NH— or —$NR_{10}$— groups or mixtures thereof and which can be unsubstituted or substituted by one or more —OH, —$OR_{10}$ or —$NH_2$ groups or mixtures thereof; or $OR_{11}$;

$R_{10}$ is straight or branched chain alkyl of 1 to 24 carbon atoms or phenyl or benzyl;

$R_{11}$ is straight or branched chain alkyl of 1 to 24 carbon atoms or phenyl or benzyl; or said alkyl substituted by one or more —OH, —OCO—$R_{10}$, —$OR_{10}$, or —$NH_2$ groups or mixtures thereof; or said alkyl interrupted by one or more —O—, —NH— or —$NR_{10}$— groups or mixtures thereof and which can be unsubstituted or substituted by one or more —OH, —$OR_{10}$ or —$NH_2$ groups or mixtures thereof;

a and b represent stoichiometric coefficients which amount independently of one another to from 1 to 5000;

$$R21-O-[CH(R20)-O]_n-R22$$
(VI)

wherein the difunctional silicone of formula (II) is crosslinked via the amine functional groups of monomer M, D or A of formula (III);

and the difunctional silicone is used in an amount ranging from 0.03 to 1.0 moles of amines of monomer M, D or A of formula (III);

Fg is the residue from at least one functional reactant grafted onto a cationic amino base polymer, wherein the functional reactant is selected from the group consisting of epoxy compounds, haloalkyl compounds, isocyanate compounds and compound containing activated olefinic double bonds;

G and T are independently derived from a monomer selected from the group consisting of diallyldimethyl ammonium chloride (DADMAC), diallyldimethyl ammonium bromide, diallyldimethyl ammonium sulfate, diallyldimethyl ammonium phosphates, dimethallyldimethyl ammonium chloride, diethylallyl dimethyl ammonium chloride, diallyl di(beta-hydroxyethyl) ammonium chloride, and diallyl di(beta-ethoxyethyl) ammonium chloride;

M, D and A are independently derived from a monomer of formula (III)

$$R_3-N(R)-R_4$$
(III)

where R, $R_3$ and $R_4$ are, independently of each other, hydrogen or $C_1$-$C_4$alkyl.

22. A cationic terpolymer according to claim 21 wherein

M, D and A of formula (I) are independently derived from a monomer selected from the group consisting of diallylamine, 2,2'-dimethyl diallylamine, 2,2'-diethyl diallylamine, 2,2'-diisopropyl diallylamine, 2,2'-dipropyl diallylamine, 2,2'-diisobutyl diallylamine, N-methyl diallylamine, N-ethyl diallylamine, 2,2'-dimethyl-N-methyl diallylamine, 2,2'-diethyl-N-methyl diallylamine, 2,2'-diisoprpyl-N-methyl diallylamine, 2,2'-dipropyl-N-methyl diallylamine, 2,2'-dimethyl-N-ethyl diallylamine, and 2,2'-diethyl-N-ethyl diallylamine;

G and T of formula (I) are independently derived from a monomer selected from the group consisting diallyldimethyl ammonium chloride, diallyldimethyl ammonium sulfate, dimethallyldimethyl ammonium chloride, diethylallyl dimethyl ammonium chloride, diallyl di(beta-hydroxyethyl) ammonium chloride, and diallyl di(beta-ethoxyethyl) ammonium chloride;

E of formula (I) is derived from a difunctional siloxane monomer of formula (II)

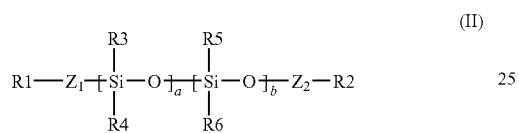

R1 and R2 independently are vinyl, allyl, methallyl, methylvinyl, acryloyl (CH2=CH—CO—), methacryloyl (CH2=C[CH3]—CO—), or epoxy;

Z1 is a direct bond or a bridging group selected from the group consisting of —O—, —((C1-C18)alkylene), —((C6-C10)arylene)-, —((C5-C8)cycloalkylene)-, -(polypropylene oxide)n-, -(polyethylene oxide)o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;

Z2 is a direct bond or a bridging group selected from the group consisting of —((C1-C18)alkylene), —((C6-C10)arylene)-, —((C5-C8)cycloalkylene)-, -(polypropylene oxide)n-, -(polyethylene oxide)o-, -(polypropylene-oxide)n(polyethylene oxide)o-, where n and o independently of one another denote numbers from 0 to 200 and the distribution of the EO/PO units can be random or in the form of blocks, —((C1-C10)alkyl)-(Si(OCH3)2)- and —(Si(OCH3)2)-;

R3, R4, R5, and R6 are independently straight or branched alkyl chain of 1 to 12 carbon atoms, cycloalkyl of 5 to 12 carbon atoms, phenyl; or said alkyl substituted by one or more —OH, —OCO—$R_{10}$, —$OR_{10}$, or —NH2 groups or mixtures thereof; or said alkyl interrupted by one or more —O—, —NH— or —$NR_{10}$— groups or mixtures thereof and which can be unsubstituted or substituted by one or more —OH, —$OR_{10}$ or —NH2 groups or mixtures thereof; or $OR_{11}$;

$R_{10}$ is straight or branched chain alkyl of 1 to 24 carbon atoms or phenyl or benzyl;

$R_{11}$ is straight or branched chain alkyl of 1 to 12 carbon atoms;

a and b represent stoichiometric coefficients which amount independently of one another to from 1 to 5000;

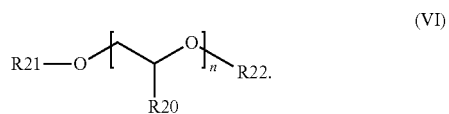

23. A cationic terpolymer according to claim 22 wherein

M, D and A of formula (I) are independently derived from a monomer selected from the group consisting of diallylamine and N-methyl diallylamine;

G and T of formula (I) are diallyldimethyl ammonium chloride;

E of formula (I) is derived from a difunctional siloxane monomer of formula (II)

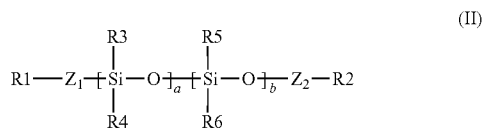

R1 and R2 independently are vinyl, allyl, methallyl, methylvinyl, acryloyl (CH2=CH—CO—), methacryloyl (CH2=C[CH3]—CO—), or epoxy;

Z1 is a direct bond or a bridging group selected from the group consisting of —((C1-C12)alkylene, —((C5-C8) cycloalkylene)-, —((C1-C10)alkyl)-(Si(OCH3)2)- and —(Si(OCH3)2)-;

Z2 is a direct bond or a bridging group selected from the group consisting of —O—, —((C1-C12)alkylene, —((C5-C8)cycloalkylene)-, —((C1-C10)alkyl)-(Si (OCH3)2)- and —(Si(OCH3)2)-;

R3, R4, R5, and R6 are independently straight or branched alkyl chain of 1 to 12 carbon atoms, phenyl; or $OR_{11}$;

$R_{11}$ is straight or branched chain alkyl of 1 to 12 carbon atoms;

a and b represent stoichiometric coefficients which amount independently of one another to from 1 to 5000;

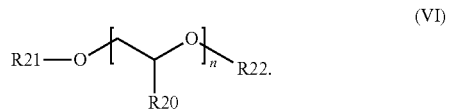

* * * * *